(12) United States Patent
Brown et al.

(10) Patent No.: US 10,266,834 B2
(45) Date of Patent: *Apr. 23, 2019

(54) RECOMBINANT RNA PARTICLES AND METHODS OF PRODUCING PROTEINS

(71) Applicant: Synthetic Genomics, Inc., La Jolla, CA (US)

(72) Inventors: Robert C. Brown, San Diego, CA (US); Kurt I. Kamrud, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,144

(22) Filed: Aug. 12, 2016

(65) Prior Publication Data
US 2017/0044555 A1    Feb. 16, 2017

Related U.S. Application Data

(60) Provisional application No. 62/204,363, filed on Aug. 12, 2015.

(51) Int. Cl.
| | |
|---|---|
| *C12N 15/113* | (2010.01) |
| *C12N 15/86* | (2006.01) |
| *C12N 15/81* | (2006.01) |
| *C12N 15/62* | (2006.01) |
| *C12N 9/62* | (2006.01) |
| *A61K 39/00* | (2006.01) |
| *A61K 39/29* | (2006.01) |
| *C12N 7/00* | (2006.01) |
| *C07K 16/10* | (2006.01) |
| *C07K 14/005* | (2006.01) |
| *C07K 14/745* | (2006.01) |
| *C07K 14/435* | (2006.01) |
| *C12N 9/78* | (2006.01) |

(52) U.S. Cl.
CPC .......... *C12N 15/81* (2013.01); *A61K 39/0005* (2013.01); *A61K 39/292* (2013.01); *C07K 14/005* (2013.01); *C07K 14/43509* (2013.01); *C07K 14/745* (2013.01); *C07K 16/1018* (2013.01); *C12N 7/00* (2013.01); *C12N 9/62* (2013.01); *C12N 9/78* (2013.01); *C12N 15/62* (2013.01); *C12Y 305/04023* (2013.01); *A61K 2039/53* (2013.01); *C07K 2317/14* (2013.01); *C07K 2317/24* (2013.01); *C12N 2720/00021* (2013.01); *C12N 2720/00034* (2013.01); *C12N 2720/00043* (2013.01)

(58) Field of Classification Search
None
See application file for complete search history.

(56) References Cited

U.S. PATENT DOCUMENTS

| | | | | |
|---|---|---|---|---|
| 2008/0069802 | A1* | 3/2008 | Davis | ................. A61K 48/0091 424/93.2 |
| 2015/0240236 | A1* | 8/2015 | Brown | ................. C12N 15/113 424/499 |

OTHER PUBLICATIONS

Caston et al. Structure of L-A Virus: A Specialized Compartment for the Transcription and Replication of Double-stranded RNA. Sep. 8, 1997. The Journal of Cell Biology. vol. 138, No. 5, pp. 975-985.*
Park et al. A Second Double-Stranded RNA Virus from Yeast. 1996. Virology. vol. 216, pp. 451-454.*
Powilleit et al. Exploiting the Yeast L-A Viral Capsid for the In Vivo Assembly of Chimeric VLPs as Platform in Vaccine Development and Foreign Protein Expression. Published on May 2, 2007. PLoS ONE. Issue 5, e415.*
Wickner, Reed B. Double-Stranded and Single-Stranded RNA Viruses of Saccharomyces Cerevisiae. Annu. Rev. Micorbiol. vol. 46, pp. 347-375. 1992.*

* cited by examiner

*Primary Examiner* — Channing S Mahatan
(74) *Attorney, Agent, or Firm* — DLA Piper LLP (US)

(57) ABSTRACT

The present invention provides compositions and methods for the production and delivery of recombinant double-stranded RNA molecules (dsRNA) encoding heterologous proteins, which can be useful for various therapeutic purposes as well as for the production of desired proteins. The compositions contain engineered double-stranded RNA particles (dsRPs) that can contain a double-stranded RNA molecule that can be a genome or portion of a genome, which can be enclosed in a capsid or coat protein. The dsRNA molecule also comprises an RNA sub-sequence that encodes a heterologous protein. The dsRPs can be derived from wild-type viral organisms. The delivery of the dsRPs (or DNA or RNA molecules) of the invention to an organism provides for therapeutic benefits as well as for the production of desired proteins.

27 Claims, 18 Drawing Sheets

Specification includes a Sequence Listing.

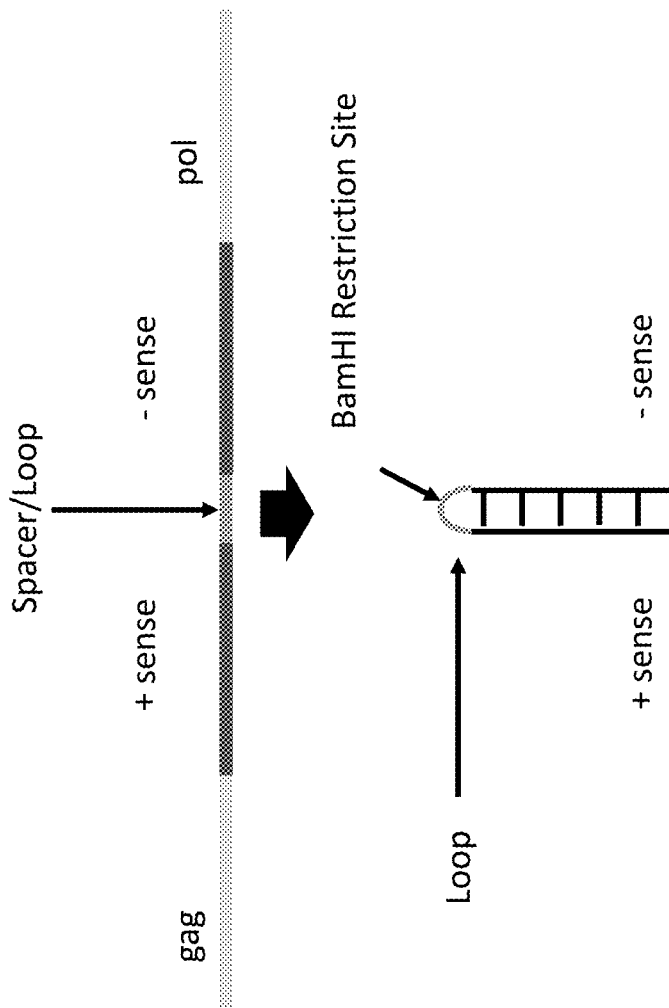

RECOMBINANT RNA PARTICLES AND METHODS OF PRODUCING PROTEINS

This application claims the benefit of U.S. Provisional Application Ser. No. 62/204,363, filed Aug. 12, 2015. The disclosure of each of the prior applications is considered part of and is incorporated by reference in the disclosure of this application.

CROSS-REFERENCE TO RELATED APPLICATIONS

U.S. application Ser. No. 14/622,671, filed Feb. 13, 2015, and U.S. Provisional Application Ser. No. 61/939,718, filed Feb. 13, 2014. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, name SGII1930-1-Sequence Listing.txt, was created on Oct. 25, 2016, and is 9 kb. The file can be assessed using Microsoft Word on a computer that uses Windows OS.

BACKGROUND

Field of Invention

The invention pertains to dsRNA particles, recombinant RNA and DNA molecules, and methods of production and use and the expression of proteins therefrom.

Background Information

Engineered viral systems present great opportunities for therapeutic and commercial applications. The genomes of many viruses have been sequenced and characterized with respect the replication, packaging, immune evasion, protective antigens, killer toxin, immunity proteins, etc. Utilizing this information, viruses have been altered for use as attenuated vaccines or engineered for use as protein expression systems for use in gene therapy, vaccines and protein products. Examples of viruses that have been used in this manner include alphaviruses, adenoviruses, baculoviruses, pox viruses, rhabdoviruses, picornaviruses, noroviruses, niedoviruses, nidoviruses, and flaviviruses.

Various methods are available for the production of proteins. Standard method of producing proteins include transformation of cells and genomic insertion of DNA by homologous or non-homologous recombination. Episomal plasmids, end joining, and artificial chromosomes or phages have also been used to get DNA into cells and to achieve transcription and translation of proteins. All of these methods are susceptible to gene silencing by epigenetic factors or by the location in the genome where the DNA happens to insert. All of these methods require the initiation of transcription and therefore positional effects in the genome, promoter strength, and gene regulation all influence their extent of expression.

It would therefore be advantageous to be able to engineer and utilize dsRNA viruses naturally found in a wide variety of yeast or fungi to deliver and/or propagate a recombinant dsRNA molecule in a virus or particle, which could be introduced into an organism to be treated to regulate gene expression in the organism or in a pathogen infecting the organism. It would also be advantageous to be able to use such systems for the production of desirable proteins or for other industrial application, such as for controlling the growth of unwanted organisms, or in the production of therapeutic agents. With such compositions and methods, a highly useful system for efficient production and delivery of packaged dsRNA could be achieved.

SUMMARY OF THE INVENTION

The present invention provides compositions and methods for the production and delivery of recombinant double-stranded RNA molecules (dsRNA) and the production of desired peptide and proteins. In one embodiment the compositions contain an engineered double-stranded RNA particle (dsRP) of the invention, but the compositions can also contain an engineered RNA or DNA molecule coding for such a dsRP. The dsRP can contain a dsRNA molecule enclosed in a capsid or coat protein. The dsRNA molecule can be a viral genome or portion of a genome, which can be derived from a wild-type viral genome. The RNA molecule can encode an RNA-dependent RNA polymerase (RDRP) and a polyprotein that forms at least part of a capsid or coat protein. The RNA molecule can also contain an RNA sub-sequence that encodes an additional, heterologous protein that is translated by the cellular components of a host cell. The protein can be heterologous to the host cell and/or to the wild-type virus the dsRP is derived from. When the dsRP (or RNA or DNA molecule) is transfected into a host cell the sub-sequence can be translated by the cellular machinery of the host cell to produce the heterologous protein. The introduction of a DNA molecule or ssRNA or dsRNA molecule as described therefore generates recombinant dsRPs and encoded proteins that can be produced under conventional conditions (e.g., yeast fermentation). The compositions are therefore useful for the production of desired proteins. The desired proteins can be useful as anti-microbials or can be proteins having a commercial or industrial value. Methods are also provided for producing protein products using the dsRP of the invention.

In a first aspect the invention provides a double-stranded RNA particle (dsRP). The dsRP can contain a recombinant double-stranded RNA molecule (dsRNA) and a capsid or coat protein, and can be able to replicate in a host cell. The RNA molecule can encode an RNA-dependent RNA polymerase and a polyprotein that forms at least part of the capsid or coat protein. The RNA molecule can further have at least one RNA sub-sequence that encodes an additional, functional protein (or merely a protein product for production) that is translated by the cellular components of the host cell. In one embodiment the dsRP is derived from a virus of the Totiviridae family. The host cell can be a yeast and the functional protein can be heterologous to the virus the dsRP is derived from. In a particular embodiment the host cell is a *Saccharomyces cerevesiae*.

In some embodiments the functional protein performs a function that affects an organism outside of the host cell, for example, inhibiting the growth of or killing a bacterial organism. The functional protein can be an enzyme that is exported from the host cell. In various embodiments the functional protein is an enzyme, for example, a cellulase, a hemicellulase, a ligninase, a lignin peroxidase, an amylase, a lipase, a mannase, a glucanase, a protease, a betaglucanase, an amyloglucosidase, a pullulanase, an acetolactate decarboxylase (ALDC), a nuclease, a DNA ligase, a polymerase, a xylanase, a papain, a rennin, a trypsin, a chymosin, a subtilisin, or a chymotrypsin.

In another embodiment the RNA sub-sequence encodes an antibody, an epitope to a B cell or T cell, or an immunostimulatory peptide. The T cell or B cell epitope can be displayed on the surface of the capsid or coat protein, or can be displayed on the surface of the host cell. The host cell can be engineered to contain human glycosylation pathways or can be engineered to produce a toxin to a target organism.

In another aspect the invention provides a method of producing a protein product in a host cell. The method includes transfecting a host cell with a dsRP having a recombinant double-stranded RNA molecule (dsRNA) and a capsid or coat protein. The RNA molecule can encode an RNA-dependent RNA polymerase and a polyprotein that forms at least part of the capsid or coat protein, and the dsRP can be able to replicate in the host cell. The RNA molecule can also have at least one RNA sub-sequence that encodes the protein product that is translated by cellular components of the host cell and that is heterologous to the host cell, thus producing the protein product. In one embodiment the method also involves a step of harvesting the protein product. The protein product can be any protein heterologous to the virus the dsRP is derived from.

In another aspect the invention provides a DNA vector having a sequence coding for a recombinant double-stranded RNA molecule (dsRNA) of the invention.

In another aspect the invention provides an RNA molecule translatable by a host cell. The RNA molecule can be any RNA molecule of the invention described herein. In one embodiment the RNA molecule encodes an RNA-dependent RNA polymerase and a polyprotein that forms at least part of a capsid or coat protein of a dsRP and, optionally, can have at least one sub-sequence of RNA that encodes an additional protein product.

In another aspect the invention provides a method of producing a protein product in a host cell. The method involves transfecting the host cell with an RNA or DNA molecule of the invention, and producing the protein product.

BRIEF DESCRIPTION OF THE DRAWINGS

FIG. 3B shows the same colonies in the centrifuge tube.

FIG. 6B: RNA analysis from Sucrose gradient ultracentrifugation samples, profile of recombinant. The upper and lower bands analyzed for Capsid and dsRNA. Lane A1. Standards (PRECISION PLUS PROTEIN™ WESTERNC™), B1. 1 kb NEB DNA Standard 2. CEN.PK2-1C p416TEF-GAG:RFP, 3. ATCC 208718 p41KanMX-TEF-GAG:RFP colony 1 top layer, 4. ATCC 208718 p41KanMX-TEF-GAG:RFP colony 1 lower layer, 5. ATCC 208718 p41KanMX-TEF-GAG:RFP colony 3 top layer. 6. ATCC 208718 control. In lanes 3 and 4 a feint dsRNA band can be observed. Obviously the overexpression of GAG:RFP monomers and subsequent dsRP assembled had little packaged genome.

FIG. 10B shows the results of knock down of the endogenous shrimp clotting protein gene by injection.

FIGS. 11A-11B, FIG. 11A illustrates an embodiment of the invention utilizing a hairpin structure. A spacer sequence that forms the hairpin loop is depicted and a first and second RNA sub-sequence is depicted that are separated by the spacer sequence and that are the reverse complement to one another and that will form the dsRNA hairpin loop structure. In this embodiment a BamHI restriction site is included in the spacer/loop. FIG. 11A also depicts the formation of the hairpin in the cytoplasm. FIG. 11B illustrates the dsRNA having the first and second RNA sub-sequences and spacer as present in the dsRP genome inside the capsid.

FIG. 12A also illustrates BSD expression (resistance phenotype) from a recombinant dsRNA genome. A plate is presented showing cell growth in wells A1-3 and B1-3, and low cell growth in wells A4-6 and B4-6 and C1-6. Saccharomyces cerevisae cultures transformed with recombinant T7 transcripts of 4.0 kb (5' UTR L-A helper: BSD: 2.5 kb Polymerase: 3' L-A UTR) or 2.0 kb (5' UTR L-A helper: BSD: 3' 0.5 kb polymerase: 3' L-A UTR) were grown (4 ml YPD media, Blast 100 μg/ml to 1000 μg/ml) for 48 hrs at 30° C. at 225 rpm, cells. FIG. 12B provides a western blot illustrating production of the desired heterologous protein. Cells were harvested by centrifugation (5000 g, room temp. 5 mins). Pellets were normalized to 0.2 $OD_{600}$ per sample in PBSE (137 mM NaCl, 2.7 mM KCl, 4.3 mM $Na_2HPO_4$, 1.47 mM $KH_2PO_4$, 10 mM EDTA). Cell suspensions were prepared for SDS-PAGE with NUPAGE® LDS Sample Buffer (4×) (Life Technologies Cat# NP0007 using the manufacturer's instructions). 1° Anti-BSD antibody (ab38307) ½000 dilution; 2° Anti-Rabbit IgG (A0545-1ML)-peroxidase conjugate.

DETAILED DESCRIPTION OF THE INVENTION

Figure 1:
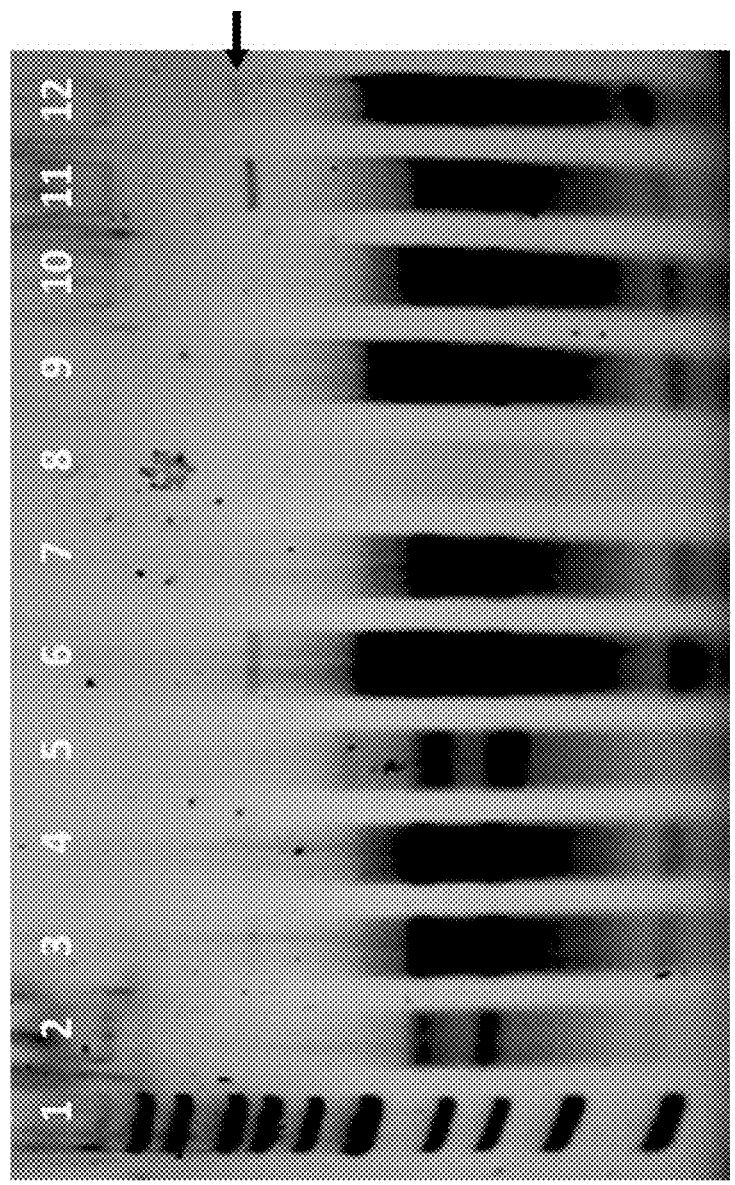
FIG. 1 illustrates agarose gel electrophoresis on 0.8% E-GEL (Life Technologies Inc.) of ATCC *Saccharomyces cerevisiae* strains total RNA preparations. Lane 1. 1 kb DNA ladder, 2. ATCC 42016, 3. ATCC 46307, 4. ATCC 208717, 5. CEN.PK2-1C, 6. ATCC 208718, 7. ATCC 44827, 8. ATCC 42015, 9. ATCC 46304, 10. ATCC 46305. 11. ATCC 42950. 12. ATCC 42017. Sample in lanes 3, 6, 9, 11 and 12 show dsRNA.

The present invention provides compositions of double-stranded RNA particles (dsRPs) and methods of use. The dsRPs contain a double-stranded RNA molecule comprised in a capsid or coat protein. The RNA molecule can be derived from a wild-type viral genome or portion of a wild-type genome. The RNA molecule encodes an RNA-dependent RNA polymerase (RDRP) and a polyprotein that forms at least part of a capsid or coat protein, and which can form the capsid or coat protein of the dsRP. The RNA molecule additionally encodes a functional protein or peptide that is translated by the host cell cellular components.

The invention provides significant advantages over standard method of producing proteins, such as ectopic or target genomic insertion of DNA by integration or recombination or homologous or non-homologous end joining, transient episomal, selective plasmids, artificial chromosomes, or phages. All of these methods are susceptible to gene silencing by epigenetic factors or by the location in the genome where they insert. All of these methods require the initiation of transcription and therefore positional effects in the genome, promoter strength, and gene regulation all influence their extent of expression. The self-replicating dsRPs (or RNA molecules or DNA molecules) of the invention are able to successfully overcome these impediments and remove these restrictions as factors because the translation of proteins is not dependent on where in the genome a DNA molecule happens to be inserted. Instead, RNA is produced within the host cell by the RNA-dependent RNA polymerase and translated into protein using the host cell's cellular machinery. Furthermore, the gene expression according to the present invention can be modulated or titrated, for example by the use of antibiotics or by counter-selection agents that rely upon dosage or copy number (e.g., zeocin). The expression from the RNA of the present invention can also be modulated or titrated by using a complimentary mechanism such as auxotrophy (e.g., with uracil, tryptophan, histidine, etc.), or by using a bradytrophic complementation system (e.g, ARG11 gene of S. cerevisiae). The expression from dsRNA can also be titrated using other metabolic complementation, for example the glyceraldehyde-3-phosphate dehydrogenase (GAPDH), isozyme 2, which is involved in glycolysis and gluconeogenesis. The enzyme is a tetramer that catalyzes the reaction of glyceraldehyde-3-phosphate to 1,3 bis-phosphoglycerate and one of the most abundant proteins in the cell. By creating a TDH2 mutation in the Saccharomyces cerevisiae or another host cell, one can rely on high level dsRNA production to complement and give consistent prototrophic growth.

The invention therefore enables the production and delivery of a recombinant dsRNA molecule that is packaged or encapsidated/encapsulated in a capsid or coat protein, and carries an RNA sub-sequence that encodes a heterologous protein or peptide. The dsRNA is packaged and amplified within a host cell (e.g., a yeast) using the same metabolic processes used by a wild-type virus (e.g., L-A virus) in the host cell. The invention does not allow for merely the translation of proteins from a plasmid or vector that has been transformed or transfected into a host cell. The dsRP of the invention can multiply in the host cells and the desired protein or peptide encoded by the RNA sub-sequence can be translated from RNA from (or sourced from) a dsRP that was previously created or amplified in a host cell culture, and not only from a plasmid or vector.

The RNA Molecule

The present invention also provides an RNA molecule encoding an RNA-dependent RNA polymerase and a polyprotein. The polyprotein can form at least a portion of a capsid or coat protein. The RNA molecule can have a sub-sequence that encodes an additional protein that is translated by host cell components when the RNA molecule is introduced into a host cell. The RNA molecule can further provide 5' and 3' untranslated regions (UTRs), which allow for the translation of the molecule inside the host cell. The UTRs can be derived from the UTRs of a wild-type virus.

The protein or peptide encoded by the sub-sequence can be heterologous to the host cell and/or to the wild-type virus from which the dsRP is derived. The protein or peptide can also be produced via translation of the nucleic acids by the cellular components of the host cell (e.g., the ribosomes, tRNA, and other protein synthesizing components necessary for protein production). The dsRNA can be encapsidated or encapsulated in the polyprotein encoded by the RNA molecule. In some embodiments the dsRNA molecule is substantially a viral genome. By being "substantially" a viral genome is meant that the sequence contains sufficient genetic information for the dsRP to autonomously replicate within a host cell. Like a wild-type genome it encodes a functioning RDRP and a polyprotein. But the genome that is substantially a viral genome can also code for an additional, heterologous protein, and can also code for UTRs. In some embodiments the polyprotein of the dsRNA molecule is a gag protein (or coat protein), which can be the major viral capsid protein. The genome that is substantially a viral genome can also encode a gag-pol fusion protein where gag encodes the major capsid protein and pol encodes a RNA-dependent RNA polymerase. In some embodiments the genome contains T7 ends to allow replication of the RNA molecule in vitro or within the host cell. In other embodiments the genome can encode additional sequences such as CRISPR guide RNA, promoters where appropriate, and dominant negative transcripts.

In other embodiments the dsRP of the invention comprises two or more dsRNA molecules of the invention comprised within the proteinaceous coat of the dsRP. The two or more dsRNA molecules can each contain one or more RNA sub-sequences encoding the additional (heterologous) protein. Thus, in one embodiment the dsRP of the invention contains two dsRNA molecules, each of which encodes a protein that is translated by the cellular components of the host cell and each of which can be substantially a viral genome.

The invention also provides a DNA plasmid or vector encoding an RNA-dependent RNA polymerase and a polyprotein described herein, and can also encode an additional (heterologous) protein, and can also encode a 5' or 3' UTR sequence derived from a wild-type virus, as described herein. The DNA plasmid or vector can encode any RNA molecule of the invention described herein, including substantially a viral genome, as described herein.

The RNA molecule of the invention (which can be substantially a viral genome) can be encapsidated within the polyprotein. The polyprotein can be a shell that surrounds or encompasses the RNA molecule of the invention. The polyprotein can comprise several oligomeric structural subunits made of proteins, called protomers. In one embodiment the polyprotein is the L-A virus major coat protein. When fully formed the polyprotein can take an icosahedral structure. In one embodiment the polyprotein comprises about 120 protomers (or about 60 dimers of the polyprotein). Once made the polyprotein can fold and so encapsidate the RNA molecule of the invention. The RNA molecule of the invention can be replicated in a host cell and can be converted into a dsRP of the invention. The dsRP can be self-replicating in the host cell.

RNA Sub-Sequence

The RNA molecule of the invention can contain at least one RNA sub-sequence that encodes a protein or peptide in addition to the RDRP and polyprotein. The protein or peptide can be a functional protein or peptide, and can be heterologous to the wild-type virus the dsRP is derived from, i.e. it is not found in the genome of the wild-type or natural virus that the dsRP is derived from, or its complementary sequence. It can also be heterologous to the host cell. The heterologous protein or peptide (or RNA sequence) may be naturally found in an organism other than the host cell and/or the virus from which the dsRP is derived. Amino acid or nucleotide sequences that are heterologous can have less than 98% or less than 95% or less than 90% or less than 80% or less than 70% or less than 60% or less than 50% or less than 40% or less than 30% or less than 20% or less than 10% sequence identity between them.

A functional protein or peptide is one that performs a biological function in or on an organism. Examples of biological functions include, but are not limited to, performing or directly participating in an enzymatic reaction, binding to a biological binding site with specificity (e.g., an antibody or immunoglobulin, a protein or peptide that binds to a receptor or to a cytokine receptor or to a gCSF receptor), transport of another molecule, or inhibiting the growth of or killing another organism. The biological function is more than just the general characteristics of any protein or peptide such as, for example, the ability to be broken down into amino acids by an organism and used for energy or for the assembly of other proteins or peptides. The heterologous protein or peptide can be a protein or peptide that performs a function that affects an organism that is not the dsRP or the host cell. The protein or peptide can also be a protein or peptide having commercial or industrial value that is produced by the methods and compositions of the invention in large quantity, e.g., at least 0.1 mg/L or at least 0.25 mg/L or at least 0.5 mg/L or at least 1.0 mg/L or at least 1 g/L or at least 3 g/L, or at least 5 g/L at least 7 g/L or at least 10 g/L. Thus, the compositions and methods of the invention can also serve as a protein/peptide expression system.

Anti-Microbial Peptides

In some embodiments the heterologous protein or peptide is an anti-microbial peptide (AMP) or a host defense peptide. These peptides can have the activity of killing or inhibiting the growth of a target microorganism or cell. Examples of such peptides include, but are not limited to, cecropins, defensins, glycine-rich peptides, proline-rich peptides, and lysozymes. Examples of target microorganisms or cells include gram negative or gram positive bacteria, enveloped viruses, fungi, and cancer cells. In some embodiments these peptide have from 12-50 amino acids or from 10-60 or from 10-80 amino acids in their active form. In some embodiments these peptide have at least 50% hydrophobic amino acid residues in their active form. In various embodiments the AMPs may interfere with DNA and protein synthesis, cell wall synthesis, or protein folding in the target microorganism or cell, or may bind intracellular proteins. In some embodiments the sub-sequence can also encode an alpha mating factor signal sequence or KEX2 cleavage site, or other sequence to inhibit activity until excreted or extruded from the host cell. Gramicidin, bacitracin, polymyxin B, vancomycin, cecropins (e.g., cecropin A, cecropin B, cecropin P1), and cecropin A(1-8)-magainin2(1-12), are some examples.

Commercial/Industrial Enzymes

In other embodiments the sub-sequence can encode an enzyme of commercial or industrial value. Examples include, but are not limited to, a cellulase, a hemicellulase, a ligninase, a lignin peroxidase, an amylase, a lipase, a mannase, a glucanase, a protease, a betaglucanase, an amyloglucosidase, a pullulanase, an acetolactate decarboxylase (ALDC), a nuclease, a DNA ligase, a polymerase, a xylanase, a papain, a rennin, a trypsin, a chymosin, a subtilisin, and a chymotrypsin. These enzymes can find use in various industrial applications such as, for example, the production of beer or wine or detergent, or in commercial baking processes, or in the processing of various forms of waste. One example of a useful enzyme that can be produced according to the invention is chymosin, or optimized versions of chymosin having at least 80% or at least 90% or at least 95% or at least 97% or at least 98% or having at least 99% or having 90-99% or 95-99% or 97-99% or 98-99% sequence identity with the natural sequence of chymosin from rennet. Compositions of these optimized sequences can have at least 50% or at least 70% or at least 80% active chymosin (w/w) compared to wild-type chymosin from rennet (which contains less than 10% active chymosin (w/w).

Antibodies

In other embodiment the RNA sub-sequence can encode an antibody for display on the surface of the host cell, or on the surface of the dsRP capsid or coat protein. The antibodies can be, for example, an IgG, a Fab, dibodies, or an scFv. Some examples of antibodies or immunoglobulins that can be produced according to the invention include, but are not limited to, AVASTIN® (bevacizumab), HUIMIRA® (adalimumab), REMICADE® (infliximab), SYNAGIS® (palivizumab), and RITUXAN®, EPOGEN® (epoetin alpha), PROCRIT® (epoetin alpha), ARANESP® (darbepoetin alfa), or colony stimulating factors (CSFs) such as NEULASTA® and NEUPOGEN®.

Glycosylation on therapeutic glycoproteins can play an important role in pharmacokinetics, efficacy and tissue targeting. By deleting a host cell's natural pathways for the glycosylation of proteins, and engineering into the host cell human glycosylation pathways, the engineered host cell can be made to express glycoprotein with human type glycans. Glycoengineered host cells (e.g., yeast) have been applied as an alternative monoclonal antibody production platform.

In other embodiments T-cell and B-cell epitopes and immunostimulatory peptides are expressed. The DNA sequence encoding the epitope or peptide can be inserted into the dsRNA molecule of the invention as a sub-sequence to create a fusion protein for the display of the epitope or peptide on the surface of the capsid protein. The epitope or peptide sequence can be inserted into the dsRNA molecule with a secretion signal and/or an internal ribosome entry site (IRES), a nucleotide sequence that allows for translation initiation in the middle of a messenger RNA (mRNA) sequence, for example cap independent mRNA translation that allows for non-gag-fusion protein expression.

The protein or peptide can also be a protein for production. Examples include proteins that are added to food products for nutritional purposes. One example is proteins added to balance or enhance the amino acid content of a food product. Proteins for production are produced in large quantities by the host cells of the invention. Some examples include vegetable proteins or plant proteins, leguminous proteins, caseins, whey proteins, wheat gluten, egg proteins, seafood proteins, canola and other oilseed proteins, mycoproteins, algal proteins.

Derived

The dsRPs of the invention can be derived from dsRNA viruses or retroviruses that are "wild-type" viruses, i.e., naturally found in yeast and fungal species. In some embodiments the dsRPs can be derived from yeast killer and/or helper viruses or from a virus of the Totiviridae family such as, for example, yeast L-A virus. These viruses are autonomously replicating, encapsidated dsRNA viruses that stably persist in the cytoplasm of a yeast or fungal cell. The helper virus (e.g. yeast L-A virus) contains a linear, non-segmented dsRNA genome (~4.6 kb) comprising two overlapping ORFs: gag protein which encodes the major capsid protein (76 kDa) and pol, a multifunctional RNA-dependent RNA polymerase (RDRP, 100 kDa). In some embodiments (e.g., when the dsRP is derived from a virus of the family Totiviridae), the dsRP can also have a third ORF. In various embodiments the dsRP is derived from a wild-type virus of the family Totiviridae, Reoviridae, Partiviridae, Chrysoviridae, or Alternaviridae. In one embodiment the dsRP is derived from the mycovirus helper virus L-A. In other embodiments the dsRP is derived from a bacteriophage φ6, or a rotavirus, or any dsRNA virus or retrovirus.

In one embodiment the dsRP (or dsRNA molecule) is derived from the dsRNA helper virus L-A, which infects *S. cerevisiae*, and the dsRNA molecule encodes substantially the genome of the L-A virus. L-A has a linear, non-segmented dsRNA genome having two overlapping ORFs—gag (76 kb) and pol. Gag encodes the major capsid protein of the virus and pol encodes the RNA-dependent RNA polymerase of the virus. The size of the native genome is approximately 4.5 kb or 4.6 kb. Within the yeast organism, pol is expressed as a gag/pol fusion protein by a −1 ribosomal frame-shift event and gag self-assembles into the capsid. In other embodiments the dsRP can be derived from a bacteriophage (e.g., bacteriophage φ6, bacteriophage T7), an alphavirus, L-BC helper virus, L-A-lus, M2, M28, M-lus, or from the M1 killer mycovirus. The dsRP can encode a dsRNA molecule derived from the genome of the virus it is derived from. In some embodiments the dsRNA of the dsRP comprises the entire wild-type or natural sequence of the virus it is derived from, but contains the additional at least one sub-sequence of RNA as described herein. The at least one RNA sub-sequence can be inserted at an appropriate locus in the wild-type or natural genome. In one embodiment when the dsRP of the invention is derived from L-A, the at least one RNA sub-sequence is inserted 3' to gag. In one embodiment a 5' untranslated region is also included. In a specific embodiment the dsRP genome comprises sequences as follows: 5'UTR-at least one RNA sub-sequence-IRE-VBS-3' UTR, where the IRE is the internal replication enhancer and VBS is the viral particle binding site.

The dsRPs of the invention can be derived from a naturally occurring virus (e.g. an RNA virus or retrovirus), meaning that the dsRNA molecule within the dsRP is the same or substantially the same as the wild type genome but also contains an RNA sub-sequence that is not contained by the wild-type virus, and which encodes a heterologous protein as described herein. In different embodiments the dsRPs of the invention have at least at least 50% or at least 60% or at least 70% or at least 80% or at least 90% or at least 95% or 80-99% or 90-99% or 95-99% or 97-99% or 98-99% or less than 100% sequence identity with the sequence of the wild type genome, not counting the RNA sub-sequence coding for the additional, heterologous protein. The dsRPs of the invention can retain in the recombinant genome the wild-type virus' ability to replicate and propagate and self-assemble in a host organism through the virus' and hot cell's natural processes. In one embodiment the dsRPs of the invention have a dsRNA molecule encapsidated by the capsid, or the dsRNA molecule is otherwise closely associated with the capsid protein. The dsRNA can be covalently bound to the capsid protein. The RNA sub-sequence can be at least 100 bp or at least 150 bp or at least 200 bp or at least 500 bp or at least 1 kb or at least 2 kb or at least 3 kb or at least 4 kb or at least 5 kb or at least 6 kb or at least 7 kb or at least 8 kb in size, or can be 100 bp-8 kb or 500 bp-8 kb or 500 bp-7 kb or 1-7 kb or 1-8 kb or 2.0-2.5 kb in size or greater than 2.5 kb.

"Derived from" a wild-type virus can also mean the dsRNA molecule of the dsRP of the invention can have at least 80% or at least 90% or at least 95% or at least 97% or at least 98% or at least 99% or 100% or 80-99% or 90-100% or 95-99% or 95-100% or 97-99% or 97-100% or 98-99% sequence identity with the wild-type RNA genome not counting the sub-sequence of RNA that encodes a heterologous protein as described herein. In one embodiment, when the virus or dsRP is derived from wild-type L-A virus, the additional sequence can be placed in between the RNA sequences for gag and pol. The same sequence identities described above can be comprised for any portion or molecule of the dsRP, for example the analogous portion of the 5' or 3' UTR).

In various embodiments the capsid protein of the derived dsRP can have at least 70% amino acid sequence identity or at least 80% amino acid sequence identity or at least 90% amino acid sequence identity or at least 95% amino acid sequence identity or at least 97% amino acid sequence identity at least 98% amino acid sequence identity or at least 99% amino acid sequence identity or 100% sequence identity with a wild-type capsid amino acid sequence. The capsid protein can also have less than 99% amino acid sequence identity or less than 95% amino acid sequence identity with the wild-type capsid protein sequence. Thus, the capsid protein of the dsRP of the invention can have from 90-99% or from 90-95% or from 95-100% or from 95-99% or from 95-98% or from or from 95-99% or from 98-100% amino acid sequence identity compared to the wild-type capsid protein, as just some examples. The same sequence identities described above can be comprised for any portion or molecule of the dsRP, for example the analogous portion of the wild-type virus RDRP.

In some embodiments the sub-sequence of RNA has at least 15 nucleotides or at least 20 nucleotides or 10-20 nucleotides or 10-30 nucleotides or 10-40 nucleotides or 10-50 nucleotides or 15-20 nucleotides or 15-30 nucleotides or 15-40 nucleotides or 15-50 nucleotides or 20-30 nucleotides or at least 50 nucleotides or at least 100 nucleotides or at least 200 nucleotides or at least 300 nucleotides or at least 500 nucleotides or at least 1000 nucleotides per single strand or 50-100 nucleotides or 50-200 nucleotides or 100-1000 nucleotides or 100-5,000 nucleotides, or can be at least 10 kb or at least 20 kb or at least 30 kb or at least 40 kb or at least 50 kb or from 10 kb-50 kb or from 30 kb to 100 kb or from 50 kb to 500 kb or from 200 kb to 1 Mb. In still more embodiments the sub-sequence of RNA can have from 100 bp-1 kb or from 1-2 kb or from 1-4 kb or from 1-8 kb or from 2-8 kb or from 4-6 kb or from 4-8 kb or from 4-9 kb.

Production of dsRP

The dsRP of the invention an also be produced by presenting to a host cell a plasmid or other DNA molecule encoding a dsRP of the invention or encoding the genes of the dsRP. The plasmid or DNA molecule is then transfected into the host cell and the host cell begins producing the dsRP of the invention. The dsRP can also be produced in the host cell by presenting to the host cell an RNA molecule encoding the genes of the dsRP. The RNA molecule can be (+)-strand RNA.

Once the dsRP of the invention has been presented to the host cell (or a plasmid encoding the genes of the dsRP of the invention, or an RNA molecule encoding the genes of the dsRP), the dsRP will be produced within the host cell using the cellular components of the host cell. The dsRP of the invention is therefore self-sustaining within the host cell and is propagated within the host cell. The host cell can be any suitable host cell such as, for example, a eukaryotic cell, a mammalian cell, a fungal cell, a bacterial cell, an insect cell, or a yeast cell, for example from the genus *Saccharomyces* (e.g., *cerevisiae*) or *Zygosaccharomyces*, or *Candida*. The host cell can propagate a recombinant dsRP after a recombinant dsRNA molecule of the invention or a DNA molecule encoding a dsRP of the invention is presented to and taken up by the host cell.

Figure 2:
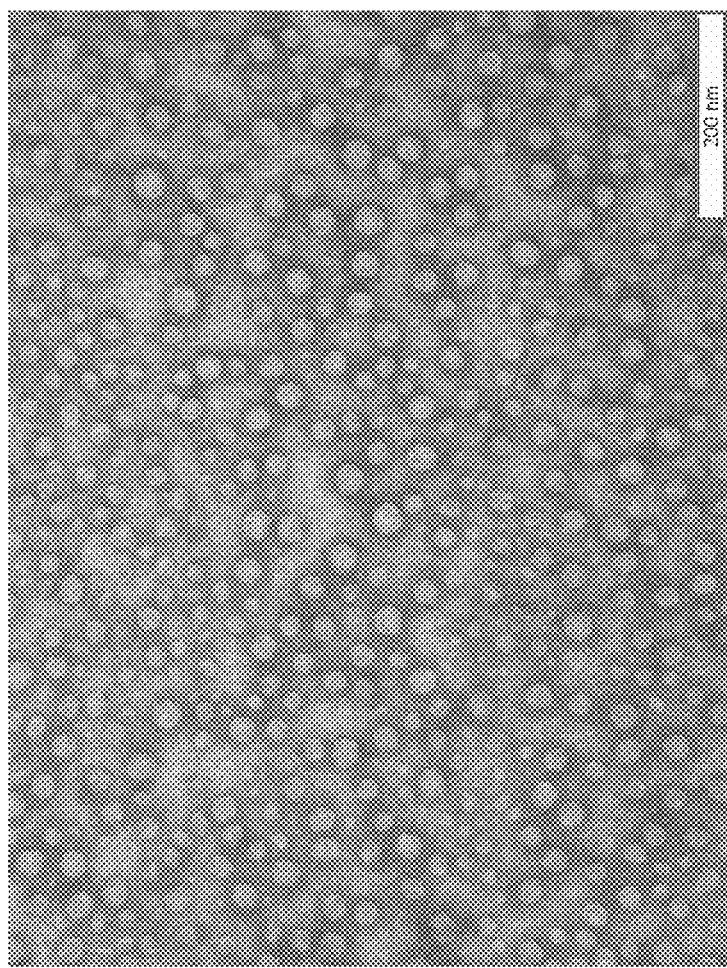
FIG. 2 shows a TEM image of capsids isolated from *Saccharomyces cerevisiae* ATCC208718.

In one embodiment the dsRPs of the present invention have a diameter of less than 100 nm. Using transmission electron microscopy (TEM) it has been determined that the present invention produces dsRPs of from about 40 to about 80 nm in diameter (FIG. 2). In various embodiments the dsRPs of the invention have a diameter of less than 90 nm or less than 80 nm or less than 70 nm or less than 60 nm or less than 50 nm, or from 30-90 nm or from 40-90 nm or from 48-80 nm or from 40-70 nm or from 40-60 nm or from 50-80 nm or 30-50 nm or 35-45 nm or about 35 nm or about 40 nm or about 45 nm or about 50 nm.

Formulations

The invention also provides a formulation containing a dsRP of the invention or containing host cells that contain a dsRP of the invention. The formulations of the invention can be useful as a vaccine or treatment. The formulations can be provided in a pharmaceutically acceptable carrier. In one embodiment the pharmaceutically acceptable carrier is phosphate buffered saline, but it can be any carrier that preserves the formulations for an acceptable period of time without causing the formulations to lose efficacy. The pharmaceutically acceptable carrier can also contain complexing agents, e.g., polycations. The compositions of the invention can also be provided in the form of a cell lysate. The formulations can be administered to treat a human or animal disease or medical condition.

Host cells contained by a formulation of the invention can be whole cells or ruptured cells, or portions thereof. The formulation can be administered by any appropriate manner, such as those described herein. The dsRP of the invention and host cells containing a dsRP of the invention are also useful in the manufacture of a medicament for the treatment of diseases, as described herein. In one embodiment host cells of the invention are transfected with a dsRP of the invention (or RNA or DNA molecule) wherein the RNA sub-sequence encodes an antibody to a target organism that causes a disease or medical condition in a human, plant, or animal. The antibody is expressed on the surface of the host cell is directed to the target organism, and the host cell is engineered to express a toxin that kills or inhibits the growth of the target organism. The antibody expressed on the surface of the host cell then directs the host cell to the target organism, which would be killed by the toxin, thus alleviating the disease or condition.

As one example, a host cell can be transfected with a dsRP (or RNA or DNA molecule encoding same) that contains a sub-sequence coding for an antibody to *Candida*. The host cell is also engineered to produce anti-*Candida* toxin. The host cell is therefore directed to the *Candida* infection and the formulation alleviates the disease or medical condition. In a particular example *H. uvarum* represents a unique L-dsRNA species encoding the secreted 18-kDa anti-*Candida* toxin, which shares homology to the toxin-coding M genomes of *S. cerevisiae*. A strategy of directed evolution can be used to produce a chimeric killer toxin that can kill *Candida* but can also be cleaved by the *Saccharomyces* host for immunity. Various IgG sequences are known that have bind specifically to *Candida albicans* cell-wall polysaccharides and glycopeptides, as well as against some protein epitopes. This strategy can therefore be used to confer protection against invasive candidiasis, or to treat such condition. In this strategy an IgG, Fab, dibodies or scFv can be coded into the dsRNA genome as the RNA sub-sequence.

In another embodiment a formulation of the invention can be used to kill or inhibit the growth of a plant fungal pathogen (e.g. fungal pathogens that affect grapes, legumes, or cereals). The host cell can be transfected with a dsRP (or RNA or DNA) containing a sub-sequence expressing a toxin against a plant fungal pathogen. The formulation can then be sprayed onto or otherwise applied to the crops. The antibody directs the host cell to the pathogen and the toxin produced by the host cell kills the pathogen.

Harvest

The dsRP particles of the invention can be harvested from the host cell. To increase dsRP yield, production can be stimulated by challenge with a non-killer strain, or by including appropriately placed wild-type constitutive/inducible promoters in the dsRNA molecule for high virus production. Host cells can also be ruptured by vortexing. The dsRP can then be conveniently harvested, purified if desired, and formulated for dosing. The physical harvesting of the dsRPs of the invention can be done by, for example, centrifugation followed by washing and re-suspension in appropriate buffer.

Induction of wild type dsRNA virus may be advantageous for the production of recombinant virus. But it is believed by the inventors that several DNA driven components (e.g., gag &/or RDRP) and recombinant ssRNA provided in trans and encoded on a DNA molecule for transcription as non-coding RNA can provide the ability to form a dsRP assembled de novo, that encapsidates RNA with specific attachment or packaging sequences. Yeast cells and total nucleic acid can also simply be harvested and formulated for the specific application. Upon harvest of the dsRP of the invention and formulation, the dsRPs can be provided to the organism to be treated to provide the protection.

Methods of Producing a dsRNA Virus or dsRP

The invention also provides methods of producing a dsRP of the invention. A double-stranded or single-stranded RNA or DNA molecule can be presented to a host cell. The amplification of the dsRNA molecules in the host cell utilizes the natural production and assembly processes already present in many types of host cells (e.g., yeast). The invention can thus be applied by presenting to a host cell a single-stranded or double-stranded RNA or DNA molecule of the invention, which is taken up by the host cell and is utilized to produce the recombinant dsRP and protein or peptide encoded by the RNA sub-sequence using the host cell's cellular components. The invention can also be applied by providing to the host cell a linear or circular DNA molecule (e.g., a plasmid or vector) containing one or more sequences coding for an RNA-dependent RNA polymerase, a polyprotein that forms at least part of the capsid or coat protein of the dsRP, and a sub-sequence encoding the additional protein, or substantially a viral genome as disclosed herein.

The presentation of a dsRNA or ssRNA molecule of the invention can be performed in any suitable way such as, for example, by presenting an RNA molecule of the invention directly to the host cell as "naked" or unmodified single-stranded or double-stranded RNA. The RNA molecule can be transfected (or transformed) into a yeast, bacterial, or mammalian host cell by any suitable method, for example by electroporation, exposure of the host cell to calcium phosphate, or by the production of liposomes that fuse with the cell membrane and deposit the viral sequence inside. It can also be performed by a specific mechanism of direct introduction of dsRNA from killer viruses or heterologous dsRNA into the host cell. This step can be optimized using a reporter system, such as red fluorescent protein (RFP), or by targeting a specific constitutive gene transcript within the host cell genome. This can be done by using a target with an obvious phenotype or by monitoring by quantitative reverse transcriptase PCR (RT-PCR).

In some embodiments a DNA molecule (e.g., a plasmid or other vector) that encodes an RNA molecule of the invention is introduced into the host cell. The DNA molecule can contain a sequence coding for the RNA molecule of a dsRP of the invention. The DNA molecule can code for an entire genome of the dsRP, or a portion thereof. The DNA molecule can further code for the at least one sub-sequence of RNA that produces the additional (heterologous) protein product. The DNA sequence can also code for gag protein or gag-pol protein, and as well as any necessary or desirable promoters or other sequences supporting the expression and purpose of the molecule. The DNA molecule can be a linear DNA, a circular DNA, a plasmid, a yeast artificial chromosome, or may take another form convenient for the specific application. In any embodiment the DNA molecule can further comprise T7 ends for producing concatamers and hairpin structures, thus allowing for propagation of the virus or dsRP sequence in vitro or in the yeast host cell. The DNA molecule can be transfected or transformed into the host cell and then, using the host cellular machinery, transcribed and thus provide the dsRNA molecule having the at least one sub-sequence of RNA to the host cell. The host cell can then produce the encoded desired protein or peptide. The dsRNA can be packaged in the same manner that a wild-type virus would be, using the host cell's metabolic processes and machinery. The protein or peptide is also produced using the host cell's metabolic processes and cellular components. In some embodiments the protein or peptide is produced by incubation or fermentation of the host cell.

In some embodiments the in vitro activation of synthetic RNA can involve the use of additional helper proteins, or the "priming" of *Saccharomyces cerevisiae* before introduction of the dsRNA molecule. In one embodiment adding a viral or synthetic dsRNA molecule to the opened empty particles, with the host factor(s) and high concentrations of polyethylene glycol, results in the conservative synthesis of viral (+) ssRNA, which is specific for viral templates, but the recognized cis-acting signals may not be optimized. However the synthesis of the (+) strands into dsRNA occurs in vitro.

Therefore the methods can include providing conditions so that the host cell takes up the ssRNA or dsRNA molecule or host cell plasmid encoding for the dsRNA molecule.

Components of the host cell will then participate in the production of the dsRP and/or desired protein or peptide. By "participate" is meant that at least one step in the production of the dsRP (or desired protein or peptide) will be performed in conjunction with metabolic components, elements, or cellular "machinery" of the host cell. The "participation" also means the production of the dsRP (or desired protein or peptide) would not occur without presence and action of the host cell's metabolic components or the environment provided by the host cell. In one embodiment the metabolic component of the host cell includes Mak3p, which performs acetylation of Gag protein (the major capsid protein).

EXAMPLE 1

Host Cell Selection

Various *Saccharomyces* strains were obtained from ATCC as potential hosts or background to genomes to look at a dsRNA production system. Table 1 highlights these strains and their viral phenotypes. These strains were characterized for virus or dsRP and dsRNA production by western blot and RNA isolation from prepared capsids. Agarose gel electrophoresis showed the predominant 4.6 kb dsRNA in several strains (FIG. 1), which was confirmed by western blot analysis. Cells were normalized by cell count as a qualitative determination of capsid (76 kDa) using a specific IgG for conserved gag epitopes. The collection demonstrated a range of viral phenotypes or traits that are potentially beneficial for recombinant dsRNA and dsRP production.

TABLE 1

| *Sacch. cerevisiae* Strain | Genotype |
| --- | --- |
| CEN.PK2-1c | MATa; ura3-52; trp1-289; leu2-3, 112; his3Δ 1; MAL2-8$^C$; SUC2 |
| ATCC 44827 | MATa/MATα ade1/+ +/ade2 +/his1 |
| ATCC 42017 | |
| ATCC 42016 | MATa ade2-1 his his4-864 [KIL-S3] |
| ATCC 42950 | MATa ade-[KIL-o] |
| ATCC 46307 | MATα ura1 trp1 MEL1 GAL [KIL-k] |
| ATCC 208718 | high levels of dsRNA gal |
| ATCC 46304 | [KIL-n] |
| ATCC 42015 | MATa ade his |
| ATCC 46305 | MATα ade2-5 [KIL-k] |
| ATCC 208717 | MATa ade2-1 his4-864 [KIL-S3] |

The deposited culture collection demonstrated a range of viral phenotypes or traits that could be beneficial for recombinant dsRNA or viral or dsRP production. Capsid purification was performed based on standard protocols. Capsid isolation was improved by using a reporter system.

A series of classically derived strains was also isolated that are able to provide the necessary host cytoplasmic factors essential for efficient dsRP assembly and packaging. Transcriptomics analysis of these strains revealed the necessary genes for this phenomenon.

Analysis of Wild-Type Yeast dsRP

Whole cells producing wild type dsRNA capsid were grown and harvested. A *Saccharomyces cerevisiae* colony was inoculated into 10 ml of YPD media (2.0% Peptone, 1.0% yeast nitrogen base, 2.0% glucose), cultures were grown up at 30° C. at 225 rpm overnight. Cell pellets were harvested with approximately $1 \times 10^8$ cells per ml on a 0.45 μm filter apparatus. The filter was washed with 10 ml of 0.1 M cacodylate, pH 6.8 and cells washed off and resuspended in 10 ml of 0.1 M cacodylate buffer containing 2.5% glutaraldehyde (fixative) and fixed at room temperature 1 hour. Cells were then fixed overnight at 4° C. The fixed cells were then washed twice in 50 mM potassium phosphate buffer pH 7.5 and finally resuspended in 2 ml potassium phosphate buffer containing 0.25 mg ml$^{-1}$ of ZYMOLASE® (a yeast lytic enzyme) and incubated for 40 min at 37° C. The resulting spheroplasts were washed twice with ice cold 0.1 M cacodylate buffer, resuspended in 1.5 ml fixative, and retained at 4° C.

For capsid preparation, a *Saccharomyces cerevisiae* colony was inoculated into 10 ml of YPD (2.0% Peptone, 1.0% Yeast Nitrogen Base, and 2.0% Glucose) or SD-Uracil media and grown up at 30° C. at 225 rpm overnight. The culture was then expanded into 400 ml of respective media and grown up at 30° C. at 225 rpm overnight. Cells were harvested by 10 min centrifugation at 5,000 g (4° C.), washed in pre-chilled H$_2$O, then washed in 1 M sorbitol, and finally resuspended in 50 ml cold PBSES (150 mM NaCl, 10 mM Na$_2$HPO$_4$ pH 7.4, 10 mM EDTA, 1 M sorbitol). Subsequently, 2-mercaptoethanol (1:2,000 and 2.5 mg ZYMOLASE 20T® were added and incubated at 30° C. for 1.5 h incubation at 120 rpm.

Spheroplasts were collected by 15 min centrifugation at 5000 g (4° C.) and washed in cold PBSES. Cells were resuspended in 10 ml PBSE (150 mM NaCl, 10 mM Na$_2$HPO$_4$ pH 7.4, 10 mM EDTA) and disrupted by vortexing seven times for 1 min (with 1 min breaks in between to cool samples on ice) in the presence of 12 g glass beads (0.45-0.55 mm). The resulting extracts were supplemented with 10 ml PBSE and centrifuged at 10,000 g for 1 h (4° C.) to sediment glass beads and cell debris. The supernatant was adjusted with PBSE to 23 ml and then layered onto a cushion of 15 ml 45% sucrose. During ultracentrifugation at 69,260 g overnight (4° C.) only structures of high molecular weight pass the cushion and form a pellet. Subsequently, the cushion pellet was resuspended in 1 ml PBSE and layered onto a linear density gradient (38 ml) of 20-70% sucrose. Upon further ultracentrifugation at 76,740 g overnight (4° C.) the gradient was fractionated into 18-20 fractions (each 2 ml) while the gradient pellet was resuspended in 2 ml PBSE. Aliquots of each fraction were subjected to SDS-PAGE followed by western analysis or Coomassie blue staining. Finally, the dsRP pellet was resuspended in 100-500 ml PBSE and stored at 4° C.

Prior to TEM processing the samples were washed twice in ice cold 0.1 M cacodylate buffer, resuspended in 1.5 ml of cold 2% OsO$_4$ (Osmium tetroxide), in 0.1 M cacodylate buffer, and incubated for 1 hour on ice in a hood. Samples were rinsed 3× with H$_2$O. 1.5 ml of 2% uranyl acetate (UrAc) aq. was added, and sample was incubated at room temp for 1 hour, then rinsed 2× with H$_2$O. Surplus sample was completely removed as UrAc is slightly radioactive. The sample was dehydrated by washing with 50%, 70%, 90% and 100% EtOH, then rinsed 1× in 100% acetone and then 50% acetone/50% DURCUPAN® was added to each tube and incubated 2 hours. Then DURCUPAN® was changed to 100% and the tubes incubated overnight. DURCUPAN® 2× was also used over the next day. The tubes were baked at 60° C. for 24 hr, and sections stained with lead citrate and uranyl acetate (UrAc).

EXAMPLE 2

Synthesis and Assembly of a Recombinant dsRNA Particle

This example illustrates the synthesis of capsids containing red fluorescent protein. This was carried out by the construction of a gag-RFP fusion sequence (SEQ ID NO: 1). A series of plasmid vectors were constructed encoding the gag protein and a 3' fusion to a commercially available RFP (TagRFP, EVROGEN®, Inc.). The fusion sequence was cloned into a CEN-ARS plasmid and a 2 shuttle vector, with either a KanMX marker cassette for gentamycin resistance or a Uracil (Ura3) cassette for auxotrophic complementation.

Figures 3A, 3B:
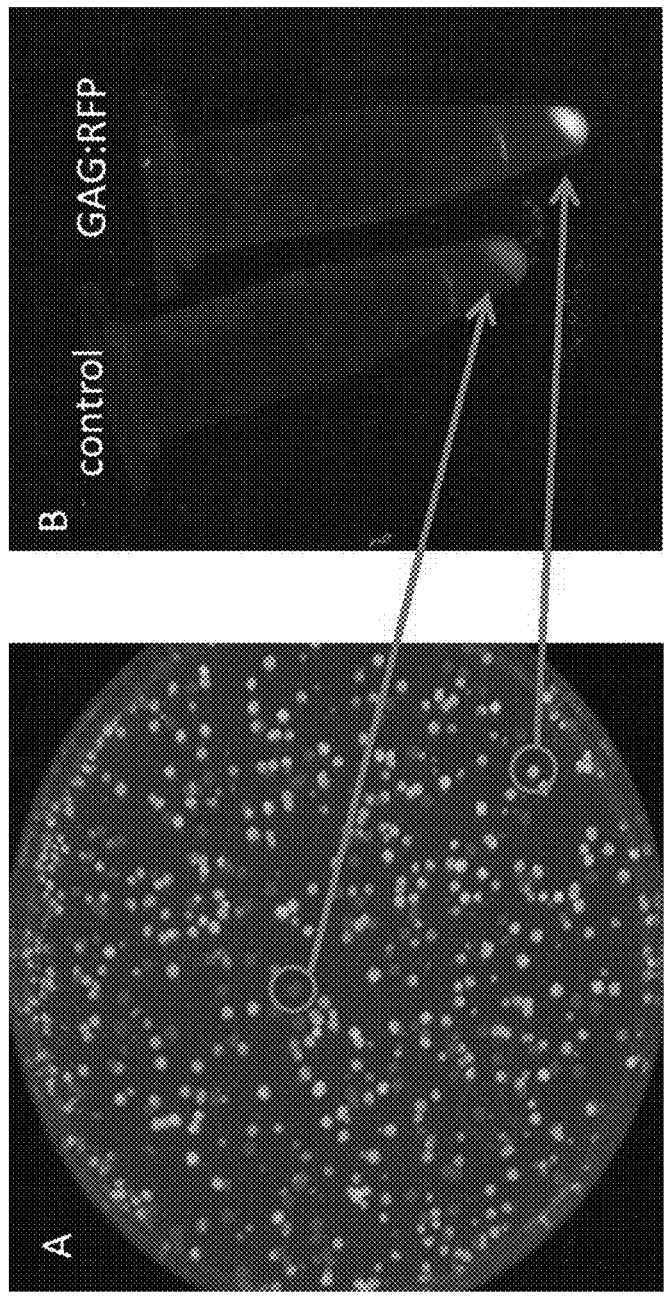
FIGS. 3A-3B, FIG. 3A shows recombinant *Saccharomyces cerevisiae* colonies transformed with GAG:RFP construct and control vector (no GAG:RFP). The fluorescent phenotype is indicative of dsRP incorporating the expressed fusion from the transformed plasmid.
Figure 4:
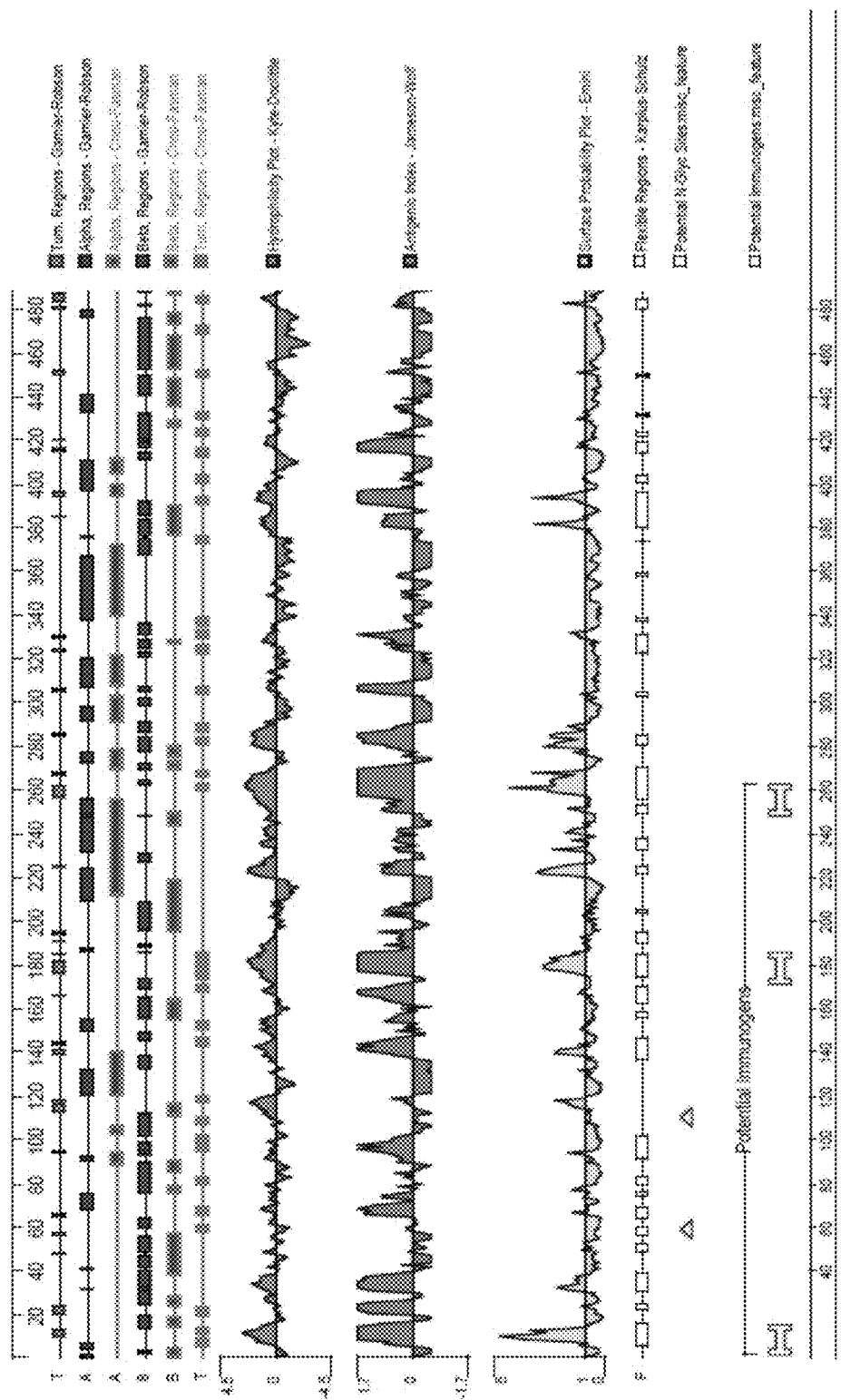
FIG. 4 provides a diagram of the first 480 amino acid residues of the GAG protein showing the hydrophobic residues for potential for exposed epitopes. Regions that maximize hydrophilicity (H), antigenicity (A), and surface probability (SP), but excluded regions that do not contain turns or that contain glycosylation sites. The H, A, and SP are evaluated on a scale of one to ten, ten being the highest. Peptide 1 at Residue 2: LRFVTKNSQDKSSD, 1 turn, H: 8, A: 7, SP: 8; Peptide 2 at Residue 172: FAWPSDRSTDSYPD, 1 turn, H: 7, A: 7, SP: 6. Peptide 3 at Residue 249: QDADEWIEGDRTDD, 1 turn, H: 7, A: 7, SP: 7. Based on these plots 3 potential peptides sequences were highlighted for synthesis and subsequent antibody production with ProSci Inc (Poway Calif.). Peptides 2 and 3 were progressed for synthesis, immunization and polyclonal IgG production.

The resultant clones had the characteristic red fluorescent colony phenotype as illustrated in FIG. 3. Colonies were cultured for production of recombinant dsRP and capsid isolation on the sucrose gradient, as detailed above. The production of recombinant capsid was validated by polyclonal IgG raised against specific peptides. The selection of peptides was based on several epitope prediction algorithms, the results of which are shown in FIG. 4.

Figure 5:
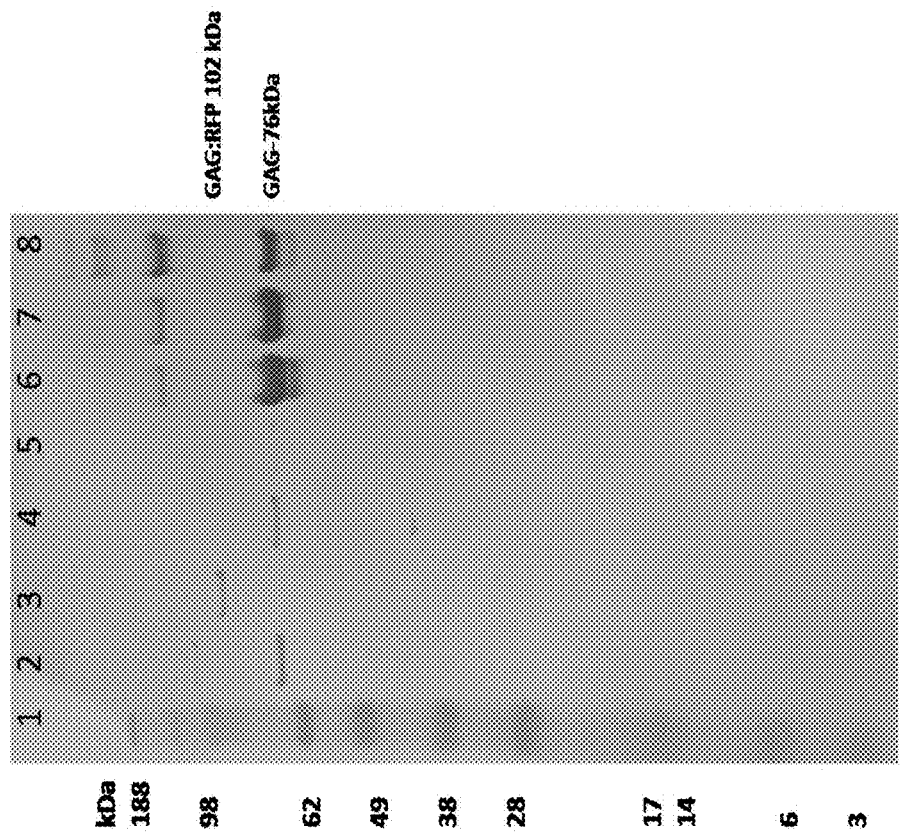
FIG. 5 illustrates a western blot of *S. cerevisiae* Capsid (GAG) protein of NUPAGE® 4-20% electrophoresis gel (Life Technologies Corp., Carlsbad, Calif.) with MES buffer Lane 1. SEEBLUE® Plus2 Pre-Stained Standard (Life Technologies Corp., Carlsbad, Calif.) Lanes 2-5. Whole cell extracts Lane 2. CEN.PK2-1C with p416TEF vector control. 3. *S. cerevisiae* CEN.PK2-1C with p416TEF-GAG:RFP. 4. ATCC 42950 5. ATCC 208718. Lanes 6-9. Sucrose gradient fractions; Lane 6. ATCC 42950, 7. ATCC 208718, 8. ATCC 46307.
Figures 6A, 6B:
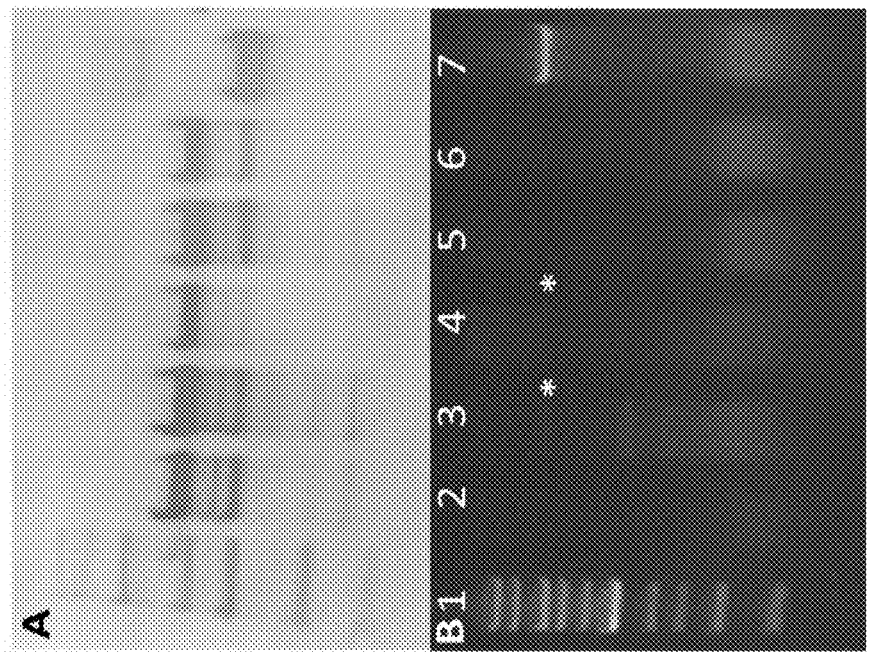
FIGS. 6A-6B, FIG. 6A illustrates A: a Western blot
Figure 7:
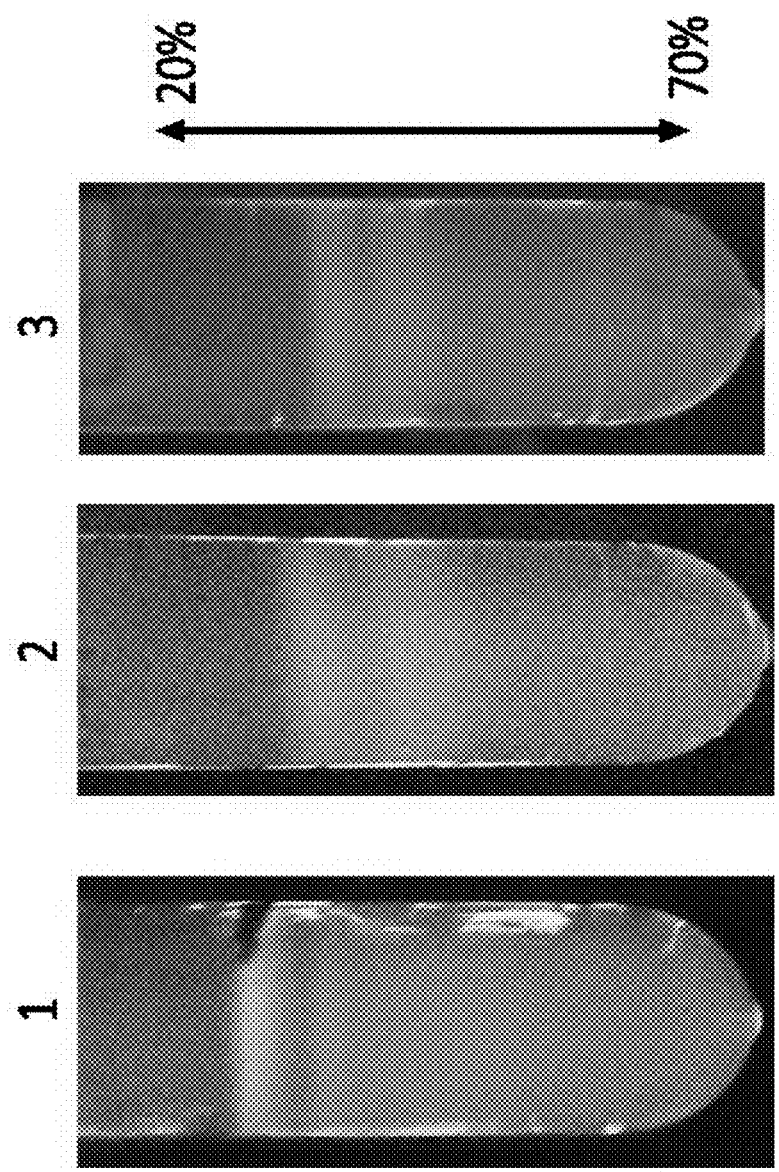
FIG. 7 is a sucrose gradient profile of recombinant *Saccharomyces cerevisiae* spheroplasts post cushion gradient (45%). Samples were fractionated into 2 red fluorescent bands on a 20-70% linear density gradient. The upper and lower bands were removed by syringe for further characterization. Sample 1. CEN.PK2-1C p416TEF-GAG:RFP, 2. ATCC 208718 p41KanMX-TEF-GAG:RFP colony 1, 3. ATCC 208718 p41KanMX-TEF-GAG:RFP colony 3.

The recombinant expressed gag:RFP fusion sequence was incorporated into the wild-type capsid assembly. The red-fluorescent dsRP was harvested via sucrose gradient. The characterization of these dsRPs was carried out by native gel electrophoresis (FIG. 5) and western blot analysis with RNA analysis (FIGS. 6A and 6B). Capsid preparations were prepared by sucrose gradient and samples resolved on native gel electrophoresis, and the sucrose gradient profile shown in FIG. 7 (which also shows the ease with which capsids can be recovered by simple use of a syringe or pipette). Samples were also submitted for TEM, which samples were adhered to grids and negatively stained using 2% uranyl acetate.

Figure 8:
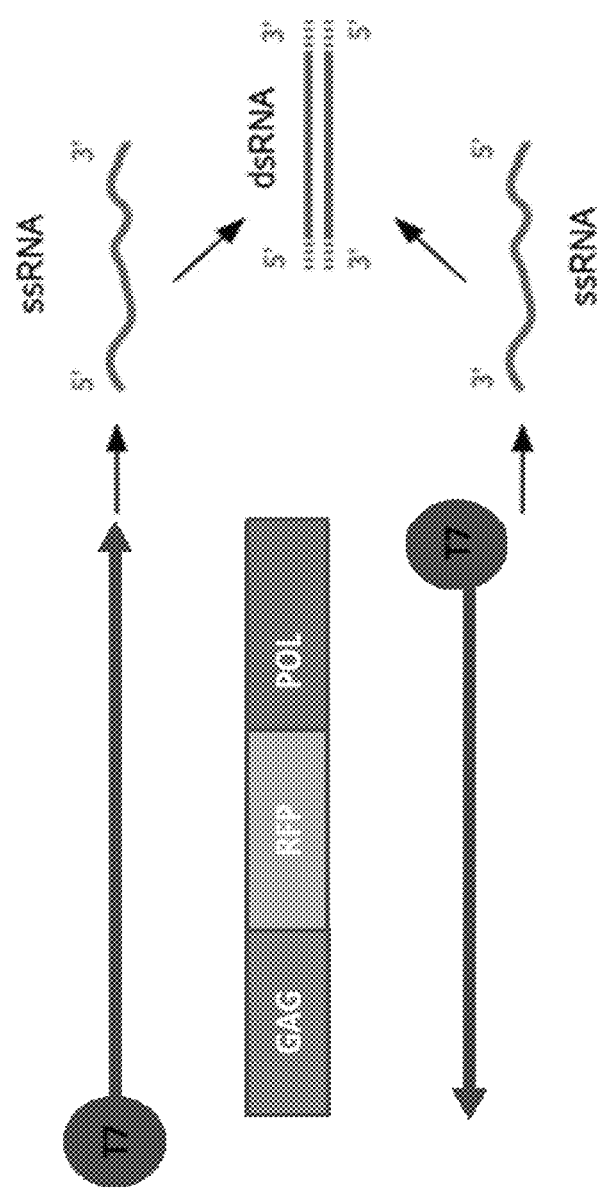
FIG. 8 is a graphical Illustration of the in vitro synthesis of a dsRNA fragment. The template for synthesis could be a plasmid or PCR fragment (including synthetic assembly). In this case the diagram depicts the synthesis of dsRNA encoding red fluorescent protein (RFP).

Double stranded RNA was synthesized by the MEGA-SCRIPT® T7 in vitro transcription kit from a genomic template with T7 ends (illustrated in FIG. 8). This was co-transformed with a selection plasmid into naïve and virus competent *Saccharomyces cerevisiae* strains. The packaged (encapsidated) recombinant dsRNA can be assembled either de novo in naïve *Saccharomyces cerevisiae*, or can be assembled and packaged in viral competent strains. After these procedures the existing native dsRNA genome will either coexist with the recombinant synthetic dsRNA, or transplant and replace the native dsRNA genome. The gel electrophoresis of control and incubated samples demonstrated the stability of dsRP preparations.

These assays demonstrated the transformation, encapsidation, and transplantation of recombinant dsRNA for both short dsRNA and a whole synthetic dsRNA genome. These assays also show that the red fluorescent dsRP has an identical or similar size and structure as the wild-type native dsRP, and that the red fluorescent dsRPs form without packaging the dsRNA viral genome.

<SEQ ID NO: 1>
Gag-RFP Fusion Protein
MLRFVTKNSQDKSSDLFSICSDRGTFVAHNRVRTDFKFDNLVFNRVYGVS

QKFTLVGNPTVCFNEGSSYLEGIAKKYLTLDGGLAIDNVLNELRSTCGIP

GNAVASHAYNITSWRWYDNHVALLMNMLRAYHLQVLTEQGQYSAGDIPMY

HDGHVKIKLPVTIDDTAGPTQFAWPSDRSTDSYPDWAQFSESFPSIDVPY

LDVRPLTVTEVNFVLMMMSKWHRRTNLAIDYEAPQLADKFAYRHALTVQD

ADEWIEGDRTDDQFRPPSSKVMLSALRKYVNHNRLYNQFYTAAQLLAQIM

MKPVPNCAEGYAWLMHDALVNIPKFGSIRGRYPFLLSGDAALIQATALED

WSAIMAKPELVFTYAMQVSVALNTGLYLRRVKKTGFGTTIDDSYEDGAFL

QPETFVQAALACCTGQDAPLNGMSDVYVTYPDLLEFDAVTQVPITVIEPA

-continued
GYNIVDDHLVVVGVPVACSPYMIFPVAAFDTANPYCGNFVIKAANKYLRK

GAVYDKLEAWKLAWALRVAGYDTHFKVYGDTHGLTKFYADNGDTWTHIPE

FVTDGDVMEVFVTAIERRARHFVELPRLNSPAFFRSVEVSTTIYDTHVQA

GAHAVYHASRINLDYVKPVSTGIQVINAGELKNYWGSVRRTQQGLGVVGL

TMPAVMPTGEPTAGAAHEELIEQADNVLVE<u>VSKGEELIKENMHMKLYMEG</u>

<u>TVNNHHFKCTSEGEGKPYEGTQTGRIKVVEGGPLPFAFDILATCFMYGSK</u>

<u>TFINHTQGIPDFFKQSFPEGFTWERVTTYEDGGVLTATQDTSLQDGCLIY</u>

<u>NVKIRGVNFPSNGPVMQKKTLGWEASTETLYPADGGLEGRCDMALKLVGG</u>

<u>GHLICNLKTTYRSKKPAKNLKMPGVYFVDRRLERIKEADNETYVEQHEVA</u>

<u>VARYCDLPSKLGHKLN</u>

The sequence above (SEQ ID NO: 1) is the amino acid sequence of gag-RFP fusion protein. The underlined text is the RFP sequence. The fusion was constructed under the control of the yeast Transcription Initiation Factor (TEF) promoter.

The material in the accompanying Sequence Listing is hereby incorporated by reference into this application.

EXAMPLE 3

DSRP Derived from L-A Virus

Figure 9:
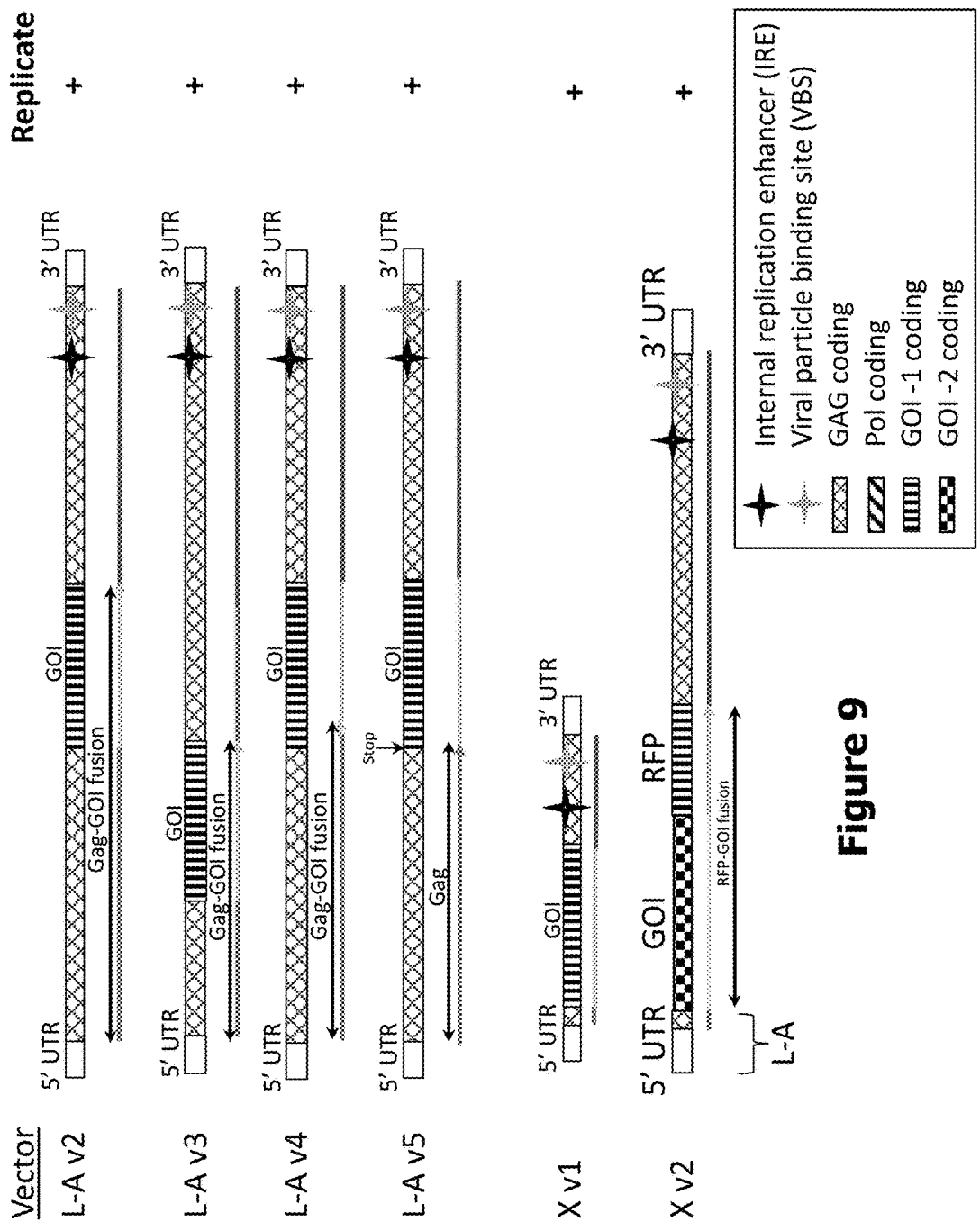
FIG. 9 is a schematic illustration of dsRNA vectors that have been examined for the ability to replicate in yeast when the gag and gag-pol proteins are provided in trans from plasmid DNA.

This example demonstrates replication of a recombinant L-A genome coding for a gag-red fluorescent protein (RFP) fusion protein (L-A v2 RFP) (FIG. 9).

In order to generate a positive sense recombinant L-A RNA with exact 5' and 3' ends, PCR primers were designed that amplified the L-A v2 RFP template with wild type 5' and 3' noncoding regions. A T7 RNA promoter was also introduced at the 5' end to support in vitro RNA transcription. A plasmid conferring uracil to yeast with uracil auxotrophy was constructed that coded for the L-A coding region without wild type 5' and 3' noncoding regions. The noncoding regions were removed so that the RNA transcript would not be replication competent yet still produce the gag and gag-pol proteins. The combinations of RNA and plasmid DNA examined in the experiment are shown in Table 2. RFP expression was detected only in cells that received both the Gag-RFP fusion recombinant RNA genome (L-A v2 RFP) and the Gag:pol plasmid DNA. In addition, RFP expression was maintained only as long as the cells remained under uracil selection indicating that the plasmid driven gag and gag-pol proteins were responsible for replicating the input recombinant genome. These data indicate that recombinant L-A genomes not only drive production of dsRNAs to induce target-specific RNAi but also express recombinant proteins of interest in yeast.

TABLE 2

| RNA/DNA transfected into yeast | RFP expression |
| --- | --- |
| L-A v2 RFP RNA | Negative |
| Gag:pol plasmid DNA | Negative |
| L-A v2 RFP RNA + Gag:pol plasmid DNA | Positive |

A representative schematic of dsRNA vectors that have been examined for the ability to replicate in yeast when the gag and gag-pol proteins are provided in trans from plasmid DNA is shown in FIG. 9. All of the recombinant dsRNAs have been shown to replicate in yeast cells.

To demonstrate that replication of recombinant RNA genomes is occurring through a dsRNA intermediate, a primer was designed to anneal to the negative strand partner of the dsRNA that could be used to generate cDNA. Because only positive sense recombinant RNA is used to transfect cells, detection of the negative sense RNA is evidence that the dsRNA replication intermediate is being generated in the yeast.

A recombinant L-A genome coding for 1100 bp of the shrimp clotting protein gene was constructed (L-A v4 clot). The L-A v4 clot construct was amplified by PCR to introduce a T7 RNA promoter as described above and positive sense RNA was produced from this template. Positive sense L-A v4 clot RNA was transfected with Gag:pol plasmid DNA into yeast with uracil auxotrophy and individual colonies were isolated. Reverse transcription PCR (RT-PCR) analysis of colonies using a negative strand RNA clot gene-specific first strand primer revealed amplification of a clot PCR product. These data indicate that a negative strand RNA was generated during replication of the input positive strand RNA.

To show that recombinant dsRNA genomes are packaged into capsids an L-A v4 clot yeast clone was grown up, the cells disrupted by microfluidization, and the material centrifuged with the supernatant was collected. Capsids in the supernatant were partially purified by pelleting through a 45% sucrose cushion. The pelleted capsid material was then loaded on to a 20-70% sucrose gradient and ultra-centrifuged overnight. A visible capsid band was collected with a needle and syringe from the 20-70% sucrose gradient and dsRNA was extracted from the purified capsids. The purified dsRNA was used to generate cDNA using random hexamers and the cDNA was submitted for sequence analysis. The complete sequence for the L-A v4 clot recombinant genome was identified in the sample, therefore confirming that the sucrose gradient purified capsid contained L-A v4 RNA.

EXAMPLE 4

Toxicity and Biodistribution

Gross toxicity and biodistribution of both purified dsRP as well as whole cell preparations was assessed as follows. For dsRP material two preparations were examined by injection in post larval pacific white shrimp (*Litopenaeus vannamei*). One preparation was purified wild type capsids collected from strain 18 yeast and the other was capsids generated by constructing a gag-RFP fusion protein gene expressed from plasmid DNA transformed into strain 18 yeast. The expressed gag-RFP fusion protein spontaneously forms capsids that contain the RFP reporter protein. The wild type and RFP capsids were either partially purified by centrifugation through a 45% sucrose cushion or further purified by centrifugation through a 20-70% sucrose gradient. The two types of capsids (wild type and RFP), from either the cushion or gradient purifications, were used to inject shrimp. No signs of toxicity were detected in any of the injected shrimp with either wild type or RFP capsid preparation.

Biodistribution was followed in RFP capsid injected animals. Red fluorescence was detected at the injection site at 2 and 6 hours post injection but could no longer be detected at the injection site by 19 hr. Gill associated RFP signal was first detected at 6 hr post injection and was evident at 19 hr post injection. As expected, animals injected with wild type capsid material showed no RFP signal at either the injection site or in gill tissue at any time point. These data indicate that the RFP capsids changed distribution from the injection site to distal locations with passage of time.

Gross biodistribution and toxicity of whole cell preparations in shrimp was also studied. The whole cell material was provided to animals in two ways 1) by provision with shrimp feed as a cold extrusion preparation (~0.2 grams wet weight yeast+~0.2 grams ground feed/alginate preparation) or 2) by simply immersing animals in water containing whole cells. The details of the whole cell shrimp exposure are summarized in Table 3.

TABLE 3

| Whole cell preparation | Feed | Immersion |
| --- | --- | --- |
| Estimated dose | ~30 mg yeast/shrimp/day | ~0.3 mg yeast/ml sea water |
| Length of exposure | Feed animals for 5 days | Day 1: Maintain shrimp in static aquarium with with heavy aeration<br>Day 2: drain yeast water replace sea water with ~0.3 mg yeast/ml sea water and maintain shrimp in static aquarium with heavy aeration |
| Time points of analysis | Day 6 | Day 3: transfer shrimp to fresh sea water and collect samples at T = 0 hr, T = 6 hr, T = 24 hr |

Animals were fed shrimp feed containing whole cell material for 5 days and samples were analyzed on day 6. As expected, no fluorescence was detected in either intestinal or gill tissues of animals fed wild type cells. Fluorescence was detected in both intestinal and gill tissues of shrimp fed whole cells containing RFP capsids. No mortalities or toxicity was noted during the time animals were fed the whole cell feed preparations.

EXAMPLE 5

Figure 10A:
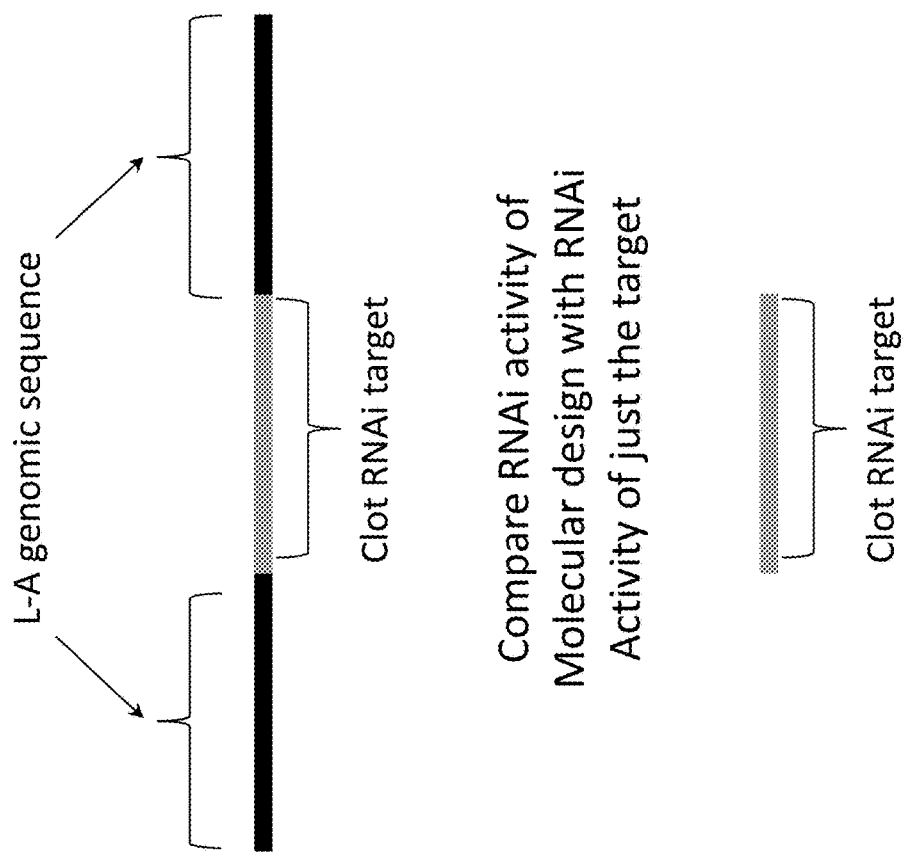
FIGS. 10A-10B, FIG. 10A is an illustration of a dsRNA molecule of the invention derived from wild-type L-A virus that can show an expected RNAi effect. Shown is an RNA sub-sequence (center) coding for the target 1100 bp of the shrimp clotting protein gene. This was constructed as L-A v5 clot.

To demonstrate that a recombinant RNA sub-sequence in the L-A genome sequence can induce an expected RNAi effect, a recombinant L-A genome coding for 1100 bp of the shrimp clotting protein gene was constructed (L-A v5 clot) (FIG. 10A). A T7 RNA promoter was engineered at both the 5' and 3' ends of individual clones so that both positive and negative sense RNAs could be in vitro transcribed as described above. In order to reconstitute a dsRNA, equal amounts of the L-A v5 clot positive and negative sense ssRNAs were combined, heat denatured and re-annealed to generate L-A v5 clot dsRNA.

Figure 10B:
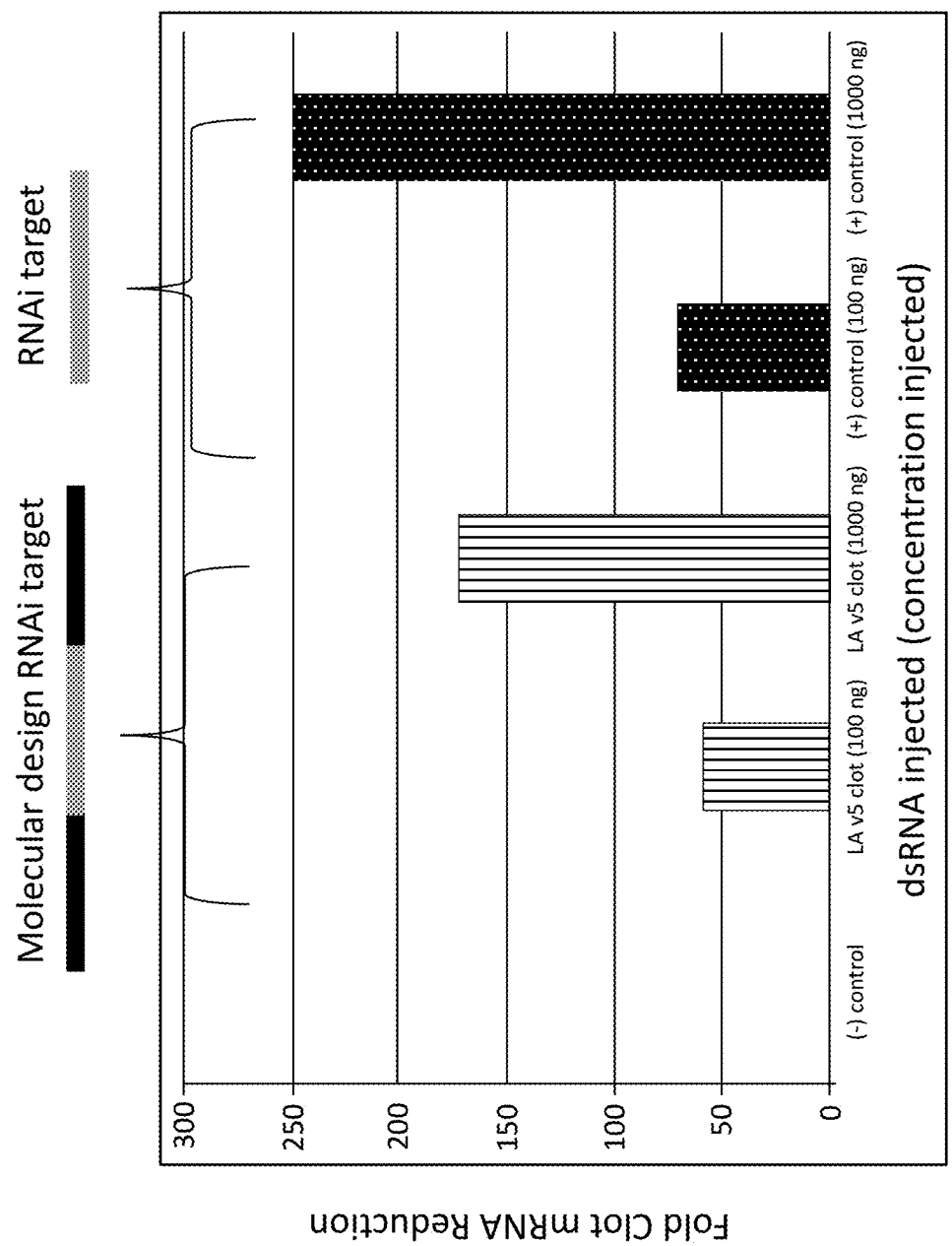
Figure 11B:
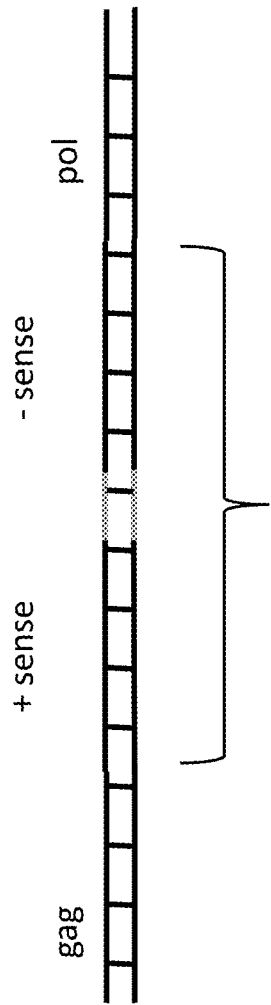

Two concentrations of L-A v5 clot dsRNA were examined for the ability to knock down the endogenous shrimp clotting protein gene by injection. Identical concentrations of the 1100 bp clot dsRNA were injected for comparison of RNAi effect on gene knock down. The fold reduction in clot gene mRNA, normalized to control for dsRNA copy number injected, for both dsRNAs is shown in FIG. 10B. The clot RNAi target in the L-A v5 clot dsRNA demonstrated very similar knock down of clot mRNA at both dsRNA concentrations injected into shrimp. These data indicate that recombinant RNAi carried by the L-A dsRNA genomes are as effective at reducing targeted genes as the RNAi target sequence is alone.

Studies designed to demonstrate that dsRP engineered to contain a portion of the shrimp clotting protein gene are capable of knocking down the endogenous shrimp clotting gene by delivering dsRP or dsRP whole cell preparations by injection, oral feeding and immersion are described in experiments 1-4 below.

EXAMPLE 6

Clot Gene Silencing

This experiment will show that administration of a vaccine formulation of the invention to pacific white shrimp results in expression of the encoded sub-sequence of the RNA molecule, which is directed to clotting protein. The control dsRP in this experiment is derived from L-A virus and is modified to contain an RNA sub-sequence encoding red fluorescent protein (RFP).

Post larval pacific white shrimp (*Litopenaeus vannamei*) (0.5-1.0 g in weight) are maintained in 10 L aquaria. The formulation was administered either by injection or orally with feed mixture or simply by inclusion in the water in which the shrimp live. When injection is the method an injection volume of 20 ul is used. Oral delivery occurs either by immersion of shrimp in seawater containing 0.3 mg yeast/ml of water or as a whole cell and ground shrimp feed mixture prepared by cold-extrusion. The estimated dose of whole yeast as a shrimp feed combination is about 30 mg/shrimp/day.

Injection Delivery Studies

Individual shrimp are vaccinated with varying doses of dsRP vaccines by injection. Initial studies examine the knock down of an endogenous shrimp clotting protein gene as a measure of how well the dsRP induces an RNAi effect with the delivered dsRNA. The relative abundance of the shrimp clotting gene mRNA is measured at varying days post injection by quantitative RT-PCR (qRT-PCR) after treatment with dsRP whole cell preparations in order to determine the duration of the RNAi knock down of the shrimp clotting protein mRNA. Injection of dsRP-RFP (red fluorescent protein) or PBS are used as the negative controls in these experiments. A 1100 bp region of the shrimp clotting gene is used to produce a dsRNA sub-sequence directed to the clotting protein mRNA, and this is used as a positive control to knock down the endogenous shrimp mRNA. Relative knock down of the endogenous clotting protein mRNA is found to be dependent on the dose of vaccine examined. That is, higher doses show higher knock down of clotting protein mRNA. Significant RNAi knock down of clotting protein mRNA is noted as late as 20 days post injection and also is dependent on the dose used. No clotting protein mRNA knock down is noted in control vaccinated animals.

Oral Delivery Studies

The ability of dsRP directed to a shrimp clotting protein to knock down the endogenous mRNA is also determined in animals for oral routes of delivery. Shrimp are exposed either by immersion or by consuming the dsRP directed to clotting protein either as whole cells in the water or as ground shrimp feed preparation containing the dsRP. Animals are immersed or fed for 10 days and then the level of clotting protein mRNA knock down is measured by qRT-PCR and compared to mRNA levels in the negative control (no treatment) and dsRP-RFP non-specific control animals. It is found that, similar to the injections studies, the level of clotting protein mRNA is reduced in animals administered the dsRP directed to clotting protein by both oral routes of delivery. Based on these results dsRP are constructed that are directed to the VP28 gene (SEQ ID NO: 71) from white spot syndrome virus (WSSV) as an RNAi target to be used in vaccination and challenge studies in shrimp.

WSSV Challenge Studies

Based on the demonstrated RNAi capability of dsRP preparations to knock down an endogenous shrimp mRNA a new dsRP specific for WSSV is synthesized and tested to show the ability of the dsRP to protect shrimp from a lethal WSSV challenge. Animals are challenged in the following manner. One shrimp not involved in the study is injected with a lethal dose of WSSV and is released into tanks of vaccinated or control animals. The WSSV injected animal succumbs to the infection in a matter of days and the vaccinated or control animals cannibalize it and thus become exposed to WSSV infection. Mortalities in the different groups are then followed over the course of the study. All animals are either immersed in or fed dsRP WSSV vaccine for 7 consecutive days. The day that shrimp are challenged is varied to include different time periods post vaccination. Animals are challenged either one day after the vaccination or 2, 4 or 9 weeks after vaccination. Significant protection from WSSV challenge is noted in all dsRP WSSV vaccinated groups even out to 9 weeks post vaccination. dsRP RFP and negative control (no treatment) groups uniformly succumb to WSSV challenge.

EXAMPLE 7

Figure 12A:
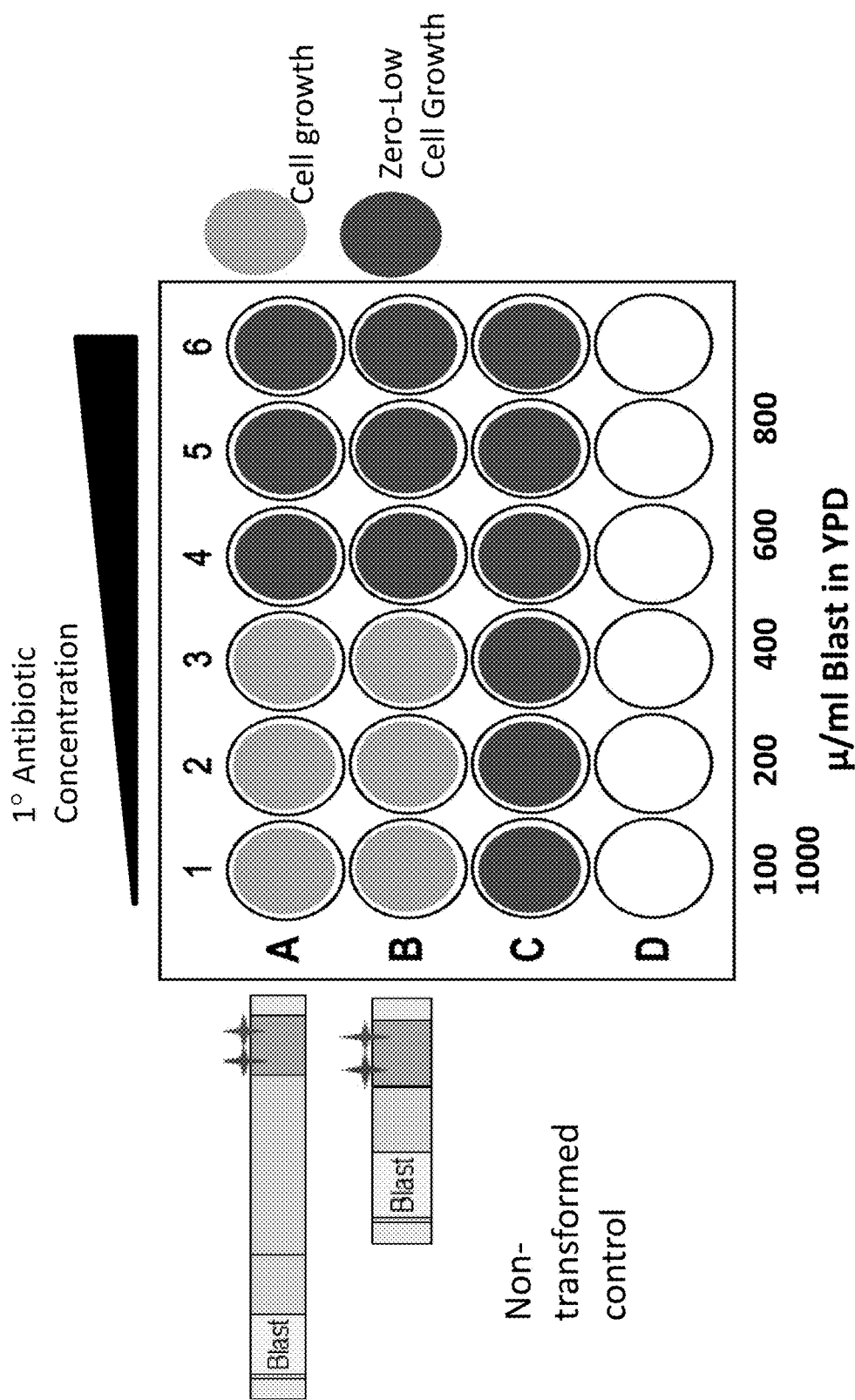
FIGS. 12A-12B, FIG. 12A illustrates a dsRNA (derived from the in vitro transcription from a PCR DNA template or linearized plasmid) of the invention encoding BSD as the heterologous protein ("Blast").
Figure 12B:
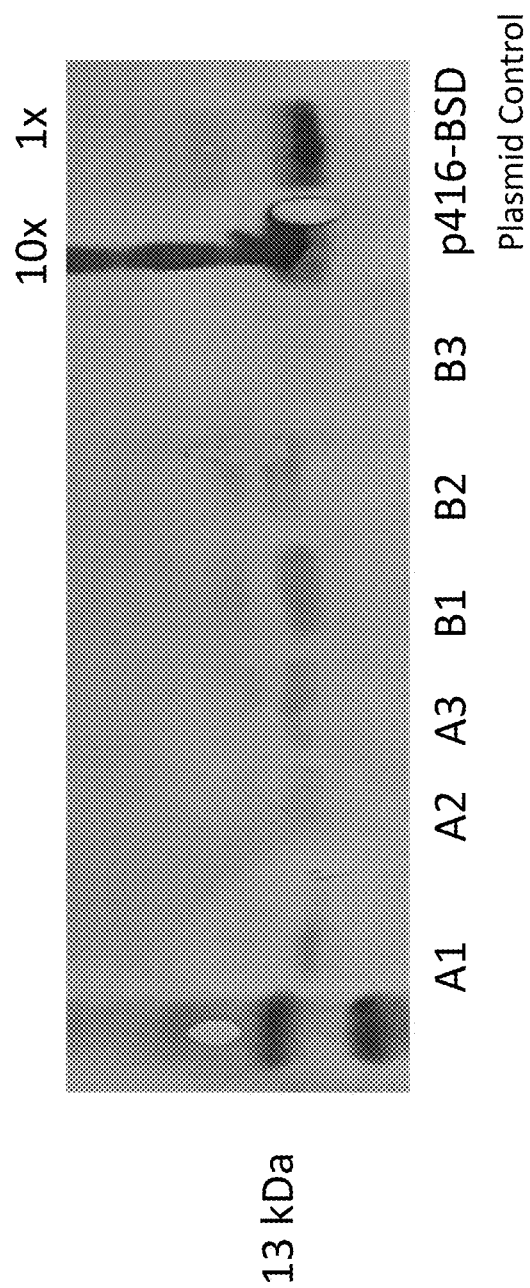
Figure 13:
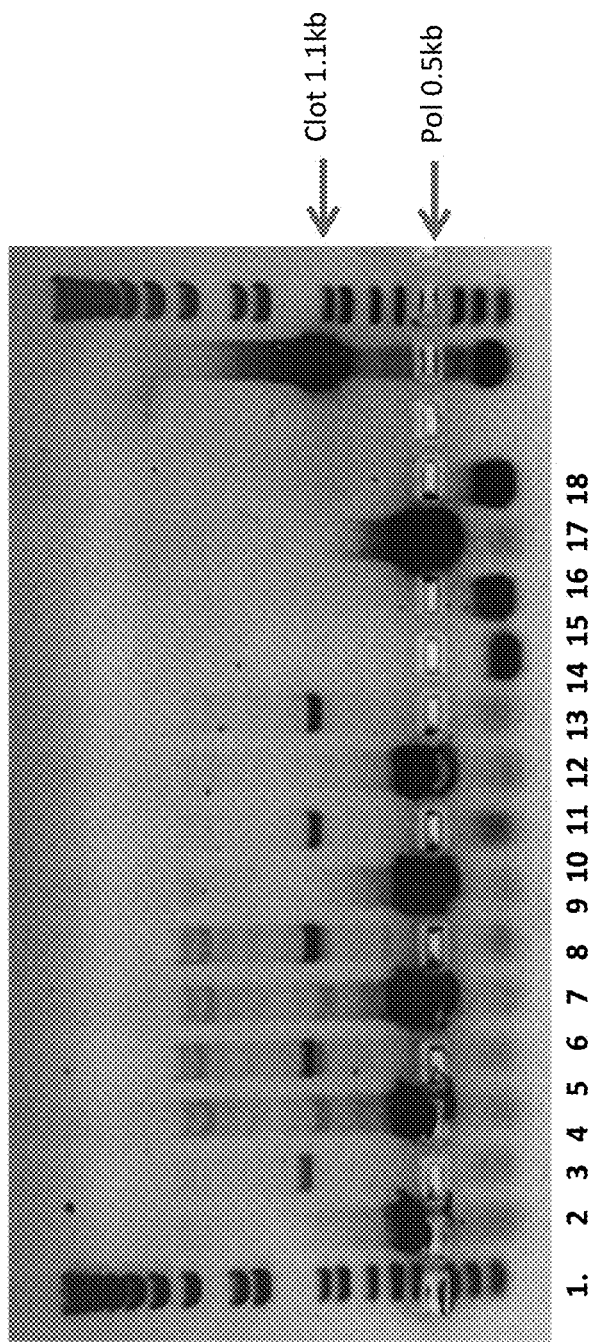
FIG. 13 provides a gel of PCR screening from cDNA derived from total cellular RNA from 50 ml cultures. Saccharomyces cerevisae cultures transformed with a recombinant T7 transcript of 2.0 kb (5' UTR LA Helper: BSD: 3' 0.5 kb Polymerase: 3' LA UTR) were grown (50 ml SD-Ura media, Blast 50μ $ml^{-1}$) for 48 hrs at 30° C. at 225 rpm; cells were harvested by centrifugation (5000 g, room temp. 5 mins). Pellets were resuspend 20% (w:v) in PBSE (137 mM NaCl, 2.7 mM KCl, 4.3 mM $Na_2HPO_4$, 1.47 mM $KH_2PO_4$, 10 mM EDTA). 1 ml of cell suspension was mixed with 600 μl phenol:chloroform:isoamyl alcohol (25:24:1, v:v) and centrifuged (21000 g, room temp. 5 mins). The aqueous phase was then extracted with Chloroform and precipitated with 30% (v:v) lithium chloride 7.5M. The RNA pellet (21000 g, room temp. 5 mins) is washed with 80% (v:v) ethanol, dried and suspended in 50 μl TE (Tris EDTA pH8.0). Lanes are as follows: 1: 1 kb plus DNA ladder; 2: 7-17 plus p416 GAG:POL 18 #1 clot PCR; 3: 7-17 plus p416 GAG:POL #1 pol PCR; 4: 7-17 plus p416 GAG:POL 18 #2 clot PCR; 5: 7-17 plus p416 GAG:POL 18 #2 pol PCR; 6: 7-17 plus p416 GAG:POL 18 #3 clot PCR; 7: 7-17 plus p416 GAG:POL 18 #3 pol PCR; 8: 7-17 plus p416 GAG:POL 18 #4 clot PCR; 9: 7-17 plus p416 GAG:POL 18 #4 pol PCR; 10: 7-17 plus p416 GAG:POL 18 #5 clot PCR; 11: 7-17 plus p416 GAG:POL 18 #5 pol PCR; 12: negative cDNA clot PCR; 13: negative cDNA pol PCR; 14: Clot DNA positive control, clot PCR; 15: Clot DNA positive control, pol PCR; 16: Pol DNA positive control, clot PCR; 17: Pol DNA positive control, pol PCR; 18: 1 kb plus DNA ladder. 10 nM RNA was used for PCR reactions for the native or recombinant RNA polymerase (0.5 kb amplicon) and a recombinant non-native shrimp clotting factor gene (1.1 kb amplicon). Standard PCR reactions (denaturation; 94° C. 30 seconds, 30 cycles (94° C. for 15-30 secs, 55° C. for 30 secs and 72° C. for 45 secs). Final extension; 72° C. for 5 minutes. Hold 4-10° C.
Figure 14:
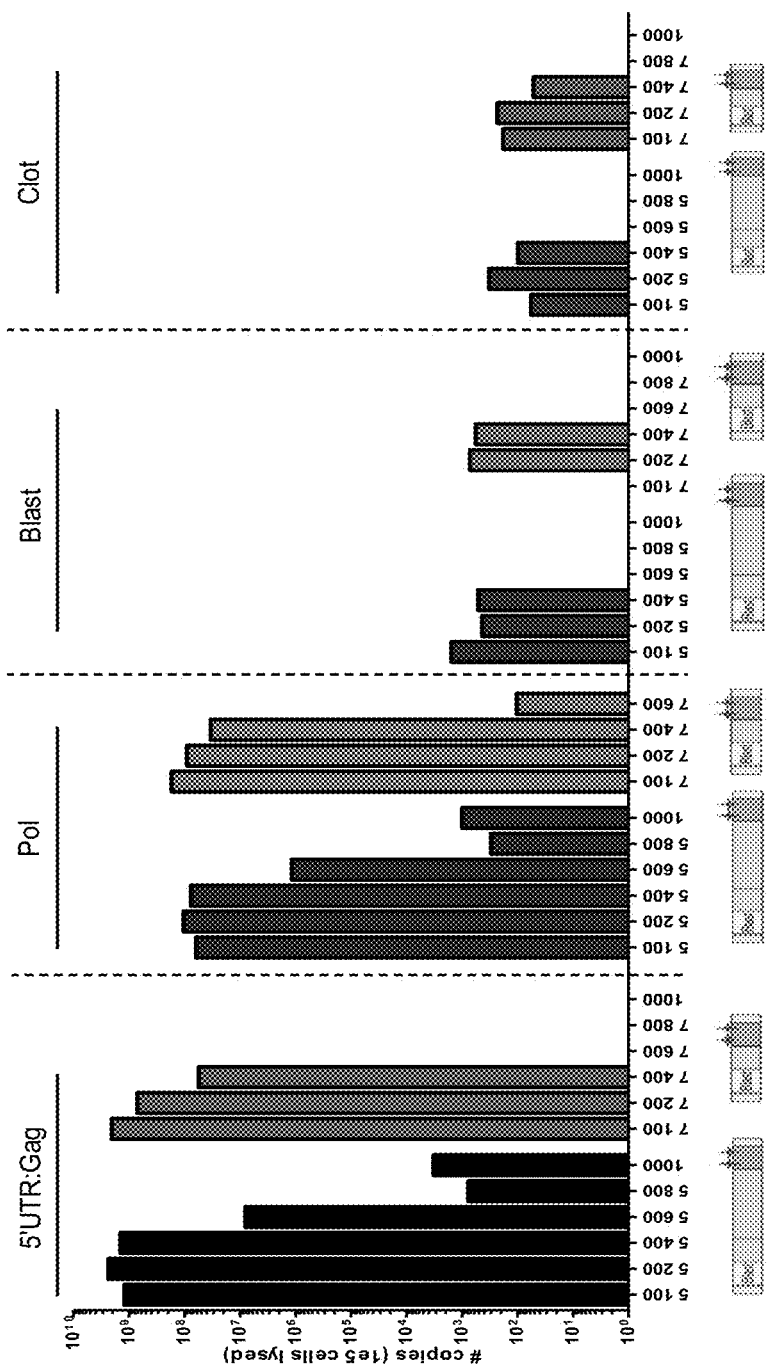
FIG. 14 provides a bar graph showing genome expression and quantitative reverse transcription PCR (qRT-PCR). Saccharomyces cerevisae cultures transformed with recombinant T7 transcripts of 4.0 kb (5' UTR L-A helper: BSD: 2.5 kb polymerase: 3' L-A UTR) or 2.0 kb (5' UTR L-A helper: BSD: 3' 0.5 kb polymerase: 3' L-A UTR). RNA prepared and probed for components of recombinant dsRNA by qRT-PCR.
Figure 15:
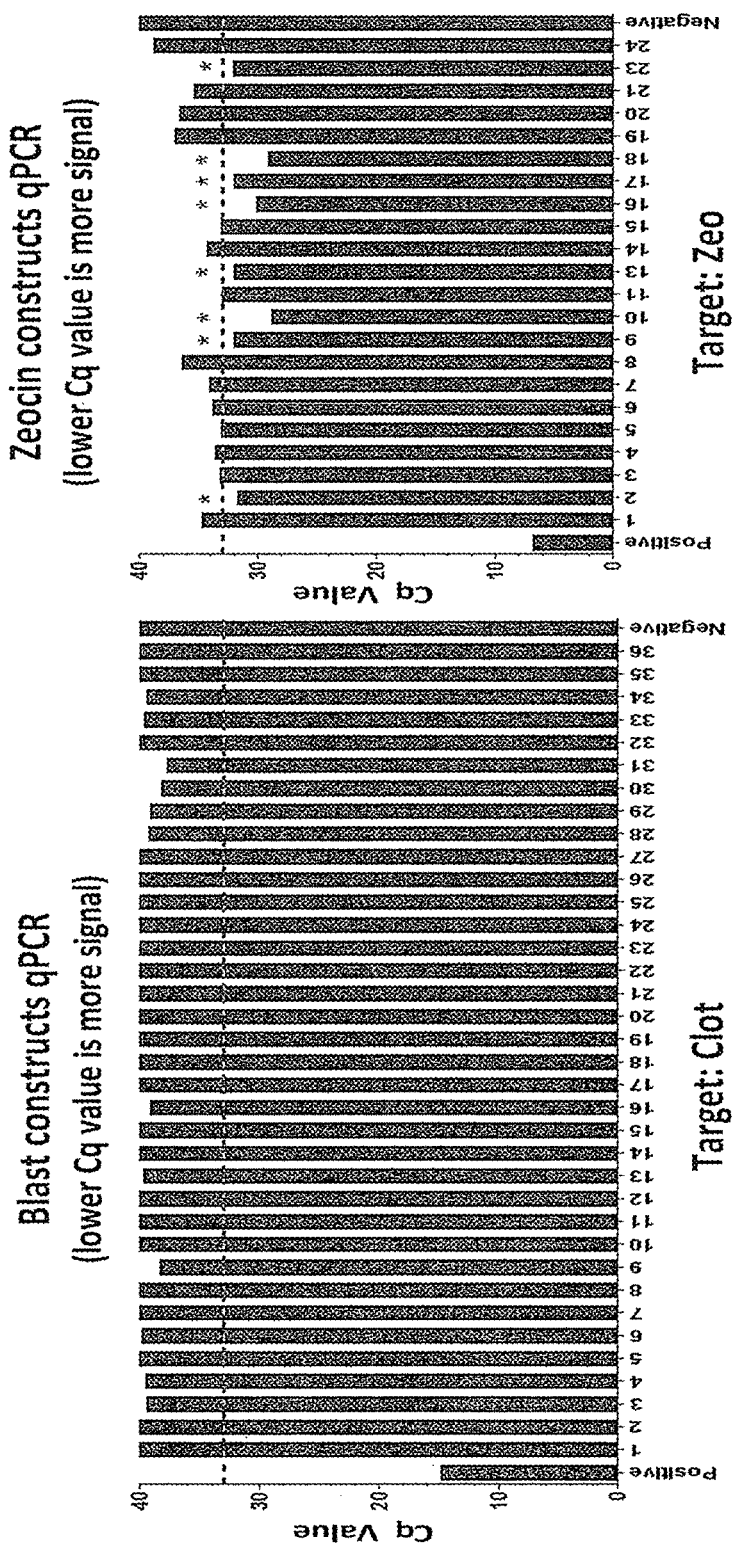
FIG. 15 provides bar graphs illustrating genome expression via quantitative reverse transcription PCR (qRT-PCR). This shows selective pressure engineered into recombinant dsRNA. Stable maintenance of recombinant dsRNAs is noted, even in the absence of selection (no antibiotic). Also seen is an increase in relative copy number of recombinant dsRNAs. Blastocidin (enzymatic action; lower copies required). Zeocin (physical action; molar copy numbers required). Copy number Zeo>Blastocidin (based on CT value).

This example shows the translation of an RNA sub-sequence in *S. cerevisiae*. A plasmid with the design illustrated in FIG. 12a was prepared. The plasmid has blasticidin S deaminase gene from *Aspergillus terreus* (BSD) as the sub-sequence to be encoded into the dsRP genome, as depicted in FIG. 12a ("Blast"). The BSD gene product has a molecular weight of approximately 13 kDa. The plasmid was introduced to *S. cerevisiae* protoplasts by utilizing a FROZEN-EZ YEAST TRANSFORMATION II KIT™ (Zymo Research Corp., Irvine, Calif.). Yeast were grown at 30° C. in 10 ml YPD broth until mid-log phase (~5×106-2×107 cells/ml or $OD_{600}$ of 0.8-1.0). The following steps were carried out at room temperature. Cells were pelleted at 500×g for 4 minutes and the supernatant discarded. 10 ml EZ 1™ solution was added to resuspend cells. Pellet the cells at 500×g and discard the supernatant. 1 ml of EZ 2™ solution was added to resuspend the pellet. At this point, the competent cells can be used for transformations directly or stored frozen at or below −70° C. for future use. For transformation (whether frozen, thawed cells or freshly prepared competent yeast cells, 50 μl of competent cells were mixed with 0.1-0.5 μg RNA (in less than 5 μl volume); 500 μl EZ 3™ solution was added and mixed thoroughly. The mixture was incubated at 30° C. for 45 minutes, and mixed vigorously by flicking with finger or vortexing (repeated 2-3 times during this incubation). 50-150 μl of the above transformation mixture was spread on an appropriate plate. The plates were incubated at 30° C. for 2-4 days to allow for growth of transformants. As illustrated in FIG. 12b, an approximately 13 kDa gene product was detected by western blot, corresponding to BSD.

EXAMPLE 8

Hepatitis B Vaccine Production

HBsAg is driven from a nuclear location, and therefore epigenetic effects can impact the long-term expression of the vaccine antigen. The present invention allows for the elimination of the epigenetic factors.

Yeast (*Saccharomyces cerevisiae*) transformed with a plasmid encoding the heptatitis B virus surface antigen gene (HBsAg) are cultured and recombinant protein is purified from disrupted cells.

De novo synthesized DNA coding for the HBsAg gene with 60 bp of L-A sequence flanking the ends of the gene is assembled by GIBSON ASSEMBLY® into different regions of the L-A genome. A positive strand RNA molecule of the invention derived from L-A virus is transcribed in vitro from a T7 RNA promoter engineered immediately upstream of the 5' UTR of the recombinant HBsAg modified L-A genome. The RNA is transfected into yeast and either the endogenous gag-pol fusion protein or a gag-pol fusion protein derived from a plasmid co-transfected with the RNA replicates and expresses the recombinant HBsAg within the cytoplasm of the transfected cell. Recombinant HBsAg is purified from transfected yeast and used as a hepatitis B vaccine antigen. Recombinant HBsAg derived from the dsRNA expression system is immunogenic and provides protection from hepatitis B infection.

EXAMPLE 9

Palivizumab Mab

Palivizumab is a humanized monoclonal antibody (IgG) directed against an epitope in the A antigenic site of the F protein of respiratory syncytial virus (RSV). De novo synthesized DNA coding for the heavy and light chains of the palivizumab monoclonal antibody is cloned into various regions of the L-A genome. Positive strand RNA is transcribed in vitro from a T7 RNA promoter engineered immediately upstream of the 5' UTR of the recombinant palivizumab L-A derived genome. The RNA is transfected into yeast and either the endogenous gag-pol fusion protein or a gag-pol fusion protein derived from a plasmid co-transformed with the RNA replicates and expresses the recombinant monoclonal antibody within the cytoplasm of the transfected cell. Recombinant anti-RSV monoclonal antibody is purified from transfected yeast and is useful for preventing the occurrence of serious lower respiratory tract disease caused by RSV in pediatric patients at high risk of developing RSV disease.

Although the invention has been described with reference to the above examples, it will be understood that modifications and variations are encompassed within the spirit and scope of the invention. Accordingly, the invention is limited only by the following claims.

What is claimed is:

1. A double-stranded RNA particle (dsRP) comprising a recombinant double-stranded RNA molecule (dsRNA) comprising,
at least one heterologous RNA sub-sequence that encodes a heterologous protein,
wherein the recombinant dsRNA molecule has at least 90% sequence identity with a wild type L-A viral genome, not counting the RNA sub-sequence that encodes the heterologous protein, and encodes a gag protein and an RNA-dependent RNA polymerase, and is sufficient for autonomous replication in a yeast host cell;
encapsidated in a capsid.

2. The dsRP of claim 1 wherein the host cell is a *Saccharomyces cerevesiae*.

3. The dsRP of claim 1 wherein the heterologous protein performs a function that affects an organism outside of the host cell.

4. The dsRP of claim 3 wherein the affect is to inhibit the growth of or kill a bacterial organism.

5. The dsRP of claim 3 wherein the heterologous protein is an enzyme that is exported from the host cell.

6. The dsRP of claim 1 wherein the heterologous protein is an enzyme selected from the group consisting of: a cellulase, a hemicellulase, a ligninase, a lignin peroxidase, an amylase, a lipase, a mannase, a glucanase, a protease, a betaglucanase, an amyloglucosidase, a pullulanase, an acetolactate decarboxylase (ALDC), a nuclease, a DNA ligase, a polymerase, a xylanase, a papain, a rennin, a trypsin, a chymosin, a subtilisin, and a chymotrypsin.

7. The dsRP of claim 1 wherein the RNA sub-sequence encodes an antibody, an epitope to a B cell or T cell, or an immunostimulatory peptide.

8. The dsRP of claim 7 wherein the RNA sub-sequence encodes an antibody.

9. The dsRP of claim 1, wherein the RNA sub-sequence encodes a T-cell or B cell epitope.

10. The dsRP of claim 9 wherein the T cell or B cell epitope is displayed on the surface of the capsid or coat protein.

11. A method of producing a protein product in a host cell comprising:
transfecting a host cell with a dsRP of claim 1,
wherein the protein product is produced.

12. The method of claim 11, further comprising harvesting the protein product.

13. The method of claim 11 wherein the host cell is a yeast.

14. The method of claim 11 wherein the dsRP is derived from a virus of the Totiviridae family.

15. The method of claim 11 wherein the RNA sub-sequence encodes a T-cell or B cell epitope, and the T cell or B cell epitope is expressed on the surface of the capsid or coat protein.

16. The method of claim 11 further comprising that the T cell or B cell epitope is expressed on the surface of the host cell.

17. The method of claim 11 wherein the protein product is an enzyme selected from the group consisting of: a cellulase, a hemicellulase, a ligninase, a lignin peroxidase, an amylase, a lipase, a mannase, a glucanase, a protease, a betaglucanase, an amyloglucosidase, a pullulanase, an acetolactate decarboxylase (ALDC), a nuclease, a DNA ligase, a polymerase, a xylanase, a papain, a rennin, a trypsin, a chymosin, a subtilisin, and a chymotrypsin.

18. A DNA vector comprising a sequence coding for a recombinant double-stranded RNA molecule (dsRNA) of claim 1.

19. An RNA molecule translatable by a host cell and encoding at least one heterologous RNA sub-sequence that encodes a heterologous protein that is translated by the host cell cellular components, and wherein the recombinant dsRNA molecule has at least 90% sequence identity with a wild type L-A viral genome, not counting the RNA sub-sequence that encodes the functional protein, and encodes a gag protein and an RNA-dependent RNA polymerase, and is sufficient for autonomous replication in a yeast host cell.

20. The RNA molecule of claim 19 comprising a viral genome.

21. The RNA molecule of claim 19 wherein the wild-type virus is an L-A virus of the Totiviridae family.

22. A method of producing a protein product in a host cell comprising:
a) transfecting the host cell with an RNA or DNA molecule encoding:
i) an RNA-dependent RNA polymerase; and
ii) a polyprotein that, when translated, forms at least part of a capsid or coat protein and creates a dsRP able to replicate in a host cell;
iii) the RNA molecule further comprising at least one heterologous RNA subsequence that encodes the protein product that is translated by cellular components of the host cell and that is heterologous to the host cell;
wherein the RNA or DNA molecule has at least 90% sequence identity with a wild type L-A virus genome, not counting the RNA sub-sequence encoding the heterologous protein product; and
b) wherein the protein product is produced.

23. The method of claim 22 wherein the host cell is a yeast.

24. The method of claim 23 wherein the dsRP is derived from a virus of the Totiviridae family and the protein product is also heterologous to the virus the dsRP is derived from.

25. The method of claim 23 wherein the RNA sub-sequence encodes a T-cell or B cell epitope, and the T cell or B cell epitope is expressed on the surface of the capsid or coat protein.

26. The method of claim 23 further comprising that the T cell or B cell epitope is expressed on the surface of the host cell.

27. The method of claim 23 wherein the protein product is an enzyme selected from the group consisting of: a cellulase, a hemicellulase, a ligninase, a lignin peroxidase, an amylase, a lipase, a mannase, a glucanase, a protease, a betaglucanase, an amyloglucosidase, a pullulanase, an acetolactate decarboxylase (ALDC), a nuclease, a DNA ligase, a polymerase, a xylanase, a papain, a rennin, a trypsin, a chymosin, a subtilisin, and a chymotrypsin.

* * * * *

```
                         SEQUENCE LISTING

<160> NUMBER OF SEQ ID NOS: 1

<210> SEQ ID NO 1
<211> LENGTH: 916
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Amino acid sequence of gag-RFP fusion protein

<400> SEQUENCE: 1

Met Leu Arg Phe Val Thr Lys Asn Ser Gln Asp Lys Ser Ser Asp Leu
1               5                   10                  15

Phe Ser Ile Cys Ser Asp Arg Gly Thr Phe Val Ala His Asn Arg Val
                20                  25                  30

Arg Thr Asp Phe Lys Phe Asp Asn Leu Val Phe Asn Arg Val Tyr Gly
            35                  40                  45

Val Ser Gln Lys Phe Thr Leu Val Gly Asn Pro Thr Val Cys Phe Asn
        50                  55                  60

Glu Gly Ser Ser Tyr Leu Glu Gly Ile Ala Lys Lys Tyr Leu Thr Leu
65                  70                  75                  80

Asp Gly Gly Leu Ala Ile Asp Asn Val Leu Asn Glu Leu Arg Ser Thr
                85                  90                  95

Cys Gly Ile Pro Gly Asn Ala Val Ala Ser His Ala Tyr Asn Ile Thr
            100                 105                 110

Ser Trp Arg Trp Tyr Asp Asn His Val Ala Leu Leu Met Asn Met Leu
        115                 120                 125

Arg Ala Tyr His Leu Gln Val Leu Thr Glu Gln Gly Gln Tyr Ser Ala
    130                 135                 140

Gly Asp Ile Pro Met Tyr His Asp Gly His Val Lys Ile Lys Leu Pro
145                 150                 155                 160

Val Thr Ile Asp Asp Thr Ala Gly Pro Thr Gln Phe Ala Trp Pro Ser
                165                 170                 175

Asp Arg Ser Thr Asp Ser Tyr Pro Asp Trp Ala Gln Phe Ser Glu Ser
            180                 185                 190
```

-continued

```
Phe Pro Ser Ile Asp Val Pro Tyr Leu Asp Val Arg Pro Leu Thr Val
        195                 200                 205

Thr Glu Val Asn Phe Val Leu Met Met Met Ser Lys Trp His Arg Arg
    210                 215                 220

Thr Asn Leu Ala Ile Asp Tyr Glu Ala Pro Gln Leu Ala Asp Lys Phe
225                 230                 235                 240

Ala Tyr Arg His Ala Leu Thr Val Gln Asp Ala Asp Glu Trp Ile Glu
                245                 250                 255

Gly Asp Arg Thr Asp Asp Gln Phe Arg Pro Ser Ser Lys Val Met
            260                 265                 270

Leu Ser Ala Leu Arg Lys Tyr Val Asn His Asn Arg Leu Tyr Asn Gln
        275                 280                 285

Phe Tyr Thr Ala Ala Gln Leu Leu Ala Gln Ile Met Met Lys Pro Val
    290                 295                 300

Pro Asn Cys Ala Glu Gly Tyr Ala Trp Leu Met His Asp Ala Leu Val
305                 310                 315                 320

Asn Ile Pro Lys Phe Gly Ser Ile Arg Gly Arg Tyr Pro Phe Leu Leu
                325                 330                 335

Ser Gly Asp Ala Ala Leu Ile Gln Ala Thr Ala Leu Glu Asp Trp Ser
            340                 345                 350

Ala Ile Met Ala Lys Pro Glu Leu Val Phe Thr Tyr Ala Met Gln Val
        355                 360                 365

Ser Val Ala Leu Asn Thr Gly Leu Tyr Leu Arg Arg Val Lys Lys Thr
    370                 375                 380

Gly Phe Gly Thr Thr Ile Asp Asp Ser Tyr Glu Asp Gly Ala Phe Leu
385                 390                 395                 400

Gln Pro Glu Thr Phe Val Gln Ala Ala Leu Ala Cys Cys Thr Gly Gln
                405                 410                 415

Asp Ala Pro Leu Asn Gly Met Ser Asp Val Tyr Val Thr Tyr Pro Asp
            420                 425                 430

Leu Leu Glu Phe Asp Ala Val Thr Gln Val Pro Ile Thr Val Ile Glu
        435                 440                 445

Pro Ala Gly Tyr Asn Ile Val Asp Asp His Leu Val Val Gly Val
    450                 455                 460

Pro Val Ala Cys Ser Pro Tyr Met Ile Phe Pro Val Ala Ala Phe Asp
465                 470                 475                 480

Thr Ala Asn Pro Tyr Cys Gly Asn Phe Val Ile Lys Ala Ala Asn Lys
                485                 490                 495

Tyr Leu Arg Lys Gly Ala Val Tyr Asp Lys Leu Glu Ala Trp Lys Leu
            500                 505                 510

Ala Trp Ala Leu Arg Val Ala Gly Tyr Asp Thr His Phe Lys Val Tyr
        515                 520                 525

Gly Asp Thr His Gly Leu Thr Lys Phe Tyr Ala Asp Asn Gly Asp Thr
    530                 535                 540

Trp Thr His Ile Pro Glu Phe Val Thr Asp Gly Asp Val Met Glu Val
545                 550                 555                 560

Phe Val Thr Ala Ile Glu Arg Arg Ala Arg His Phe Val Glu Leu Pro
                565                 570                 575

Arg Leu Asn Ser Pro Ala Phe Phe Arg Ser Val Glu Val Ser Thr Thr
            580                 585                 590

Ile Tyr Asp Thr His Val Gln Ala Gly Ala His Ala Val Tyr His Ala
        595                 600                 605
```

-continued

```
Ser Arg Ile Asn Leu Asp Tyr Val Lys Pro Val Ser Thr Gly Ile Gln
    610                 615                 620
Val Ile Asn Ala Gly Glu Leu Lys Asn Tyr Trp Gly Ser Val Arg Arg
625                 630                 635                 640
Thr Gln Gln Gly Leu Gly Val Val Gly Leu Thr Met Pro Ala Val Met
                645                 650                 655
Pro Thr Gly Glu Pro Thr Ala Gly Ala Ala His Glu Glu Leu Ile Glu
                660                 665                 670
Gln Ala Asp Asn Val Leu Val Glu Val Ser Lys Gly Glu Glu Leu Ile
            675                 680                 685
Lys Glu Asn Met His Met Lys Leu Tyr Met Glu Gly Thr Val Asn Asn
    690                 695                 700
His His Phe Lys Cys Thr Ser Glu Gly Glu Gly Lys Pro Tyr Glu Gly
705                 710                 715                 720
Thr Gln Thr Gly Arg Ile Lys Val Val Glu Gly Gly Pro Leu Pro Phe
                725                 730                 735
Ala Phe Asp Ile Leu Ala Thr Cys Phe Met Tyr Gly Ser Lys Thr Phe
            740                 745                 750
Ile Asn His Thr Gln Gly Ile Pro Asp Phe Phe Lys Gln Ser Phe Pro
    755                 760                 765
Glu Gly Phe Thr Trp Glu Arg Val Thr Thr Tyr Glu Asp Gly Gly Val
    770                 775                 780
Leu Thr Ala Thr Gln Asp Thr Ser Leu Gln Asp Gly Cys Leu Ile Tyr
785                 790                 795                 800
Asn Val Lys Ile Arg Gly Val Asn Phe Pro Ser Asn Gly Pro Val Met
                805                 810                 815
Gln Lys Lys Thr Leu Gly Trp Glu Ala Ser Thr Glu Thr Leu Tyr Pro
            820                 825                 830
Ala Asp Gly Gly Leu Glu Gly Arg Cys Asp Met Ala Leu Lys Leu Val
            835                 840                 845
Gly Gly Gly His Leu Ile Cys Asn Leu Lys Thr Thr Tyr Arg Ser Lys
    850                 855                 860
Lys Pro Ala Lys Asn Leu Lys Met Pro Gly Val Tyr Phe Val Asp Arg
865                 870                 875                 880
Arg Leu Glu Arg Ile Lys Glu Ala Asp Asn Glu Thr Tyr Val Glu Gln
                885                 890                 895
His Glu Val Ala Val Ala Arg Tyr Cys Asp Leu Pro Ser Lys Leu Gly
            900                 905                 910
His Lys Leu Asn
    915
```